(12) United States Patent
Gavai et al.

(10) Patent No.: US 7,102,003 B2
(45) Date of Patent: Sep. 5, 2006

(54) PYRROLOTRIAZINE COMPOUNDS

(75) Inventors: Ashvinikumar V. Gavai, Princeton Junction, NJ (US); Harold Mastalerz, Guilford, CT (US); Jean-Paul Daris, St-Hubert (CA); Pierre Dextraze, Laprarie (CA); Philippe Lapointe, Greenfield Park (CA); Edward H. Ruediger, Greenfield Park (CA); Dolatrai M. Vyas, Madison, CT (US); Guifen Zhang, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/157,460

(22) Filed: Jun. 21, 2005

(65) Prior Publication Data

US 2006/0014745 A1    Jan. 19, 2006

Related U.S. Application Data

(60) Provisional application No. 60/584,768, filed on Jul. 1, 2004.

(51) Int. Cl.
C07D 487/04  (2006.01)
A61K 31/53   (2006.01)
A61P 35/00   (2006.01)

(52) U.S. Cl. ................................ 544/183; 514/243
(58) Field of Classification Search ............... 544/183; 514/243
See application file for complete search history.

(56) References Cited

U.S. PATENT DOCUMENTS

| | | | |
|---|---|---|---|
| 6,670,357 B1 | 12/2003 | Leftheris et al. |
| 6,787,545 B1 | 9/2004 | Ohtani et al. |
| 6,867,300 B1 | 3/2005 | Godfrey, Jr. et al. |
| 6,869,952 B1 | 3/2005 | Bhide et al. |
| 6,908,916 B1 | 6/2005 | Mastalerz et al. |
| 6,916,815 B1 | 7/2005 | Vite et al. |
| 2003/0232831 A1 | 12/2003 | Dyckman et al. |
| 2003/0232832 A1 | 12/2003 | Lombardo et al. |
| 2004/0063707 A1 | 4/2004 | Bhide et al. |
| 2004/0063708 A1 | 4/2004 | Bhide et al. |
| 2004/0077858 A1 | 4/2004 | Bhide et al. |
| 2004/0229877 A1 | 11/2004 | Leftheris et al. |

FOREIGN PATENT DOCUMENTS

| | | |
|---|---|---|
| EP | 0 713 876 | 5/1996 |
| WO | WO 98/08847 | 3/1998 |
| WO | WO 00/71129 | 11/2000 |
| WO | WO 02/40486 | 5/2002 |
| WO | WO 03/090912 | 11/2003 |
| WO | WO 2004/009784 | 1/2004 |

OTHER PUBLICATIONS

Cecil Textbook of Medicine, edited Bennet, J.C., and Plum F., 20th edition, vol. 1, 1004-1010, 1996.*
Wolft Manfréd E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Tsi-Ping et al., TIPS 16: 5766, 1995.*
West, Anthony R., Solid State Chemistry and its Applications, Wiley, New York, 1988, pp. 358 & 365.*
Vippagunta et al., Advanced Drug Delivery Reviews 48: 3-26, 2001.*
U.S. Appl. No. 60/620,784, filed Oct. 21, 2004, Gavai et al.
U.S. Appl. No. 11/008,719, filed Dec. 9, 2004, Swaminathan et al.
U.S. Appl. No. 11/019,899, filed Dec. 22, 2004, Gavai et al.
U.S. Appl. No. 11/019,901, filed Dec. 22, 2004, Fink et al.
U.S. Appl. No. 11/152,650, filed Jun. 14, 2005, Cai et al.
Ewald, H. et al., "Reaktionen von 1,2,4-Triazinen mit Acetylendicarbonsäure-dimethylester", Liebigs Ann. Chem., pp. 1718-1724 (1977).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).

* cited by examiner

*Primary Examiner*—Venkataraman Balasubramanian
(74) *Attorney, Agent, or Firm*—Elliott Korsen

(57) ABSTRACT

The present invention provides compounds of formula I

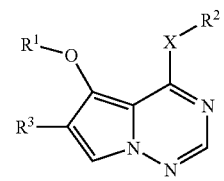

and pharmaceutically acceptable salts thereof.

The compounds of the invention inhibit tyrosine kinase activity of growth factor receptors such as HER1, HER2 and HER4 thereby making them useful as antiproliferative agents. The compounds are also useful for the treatment of other diseases associated with signal transduction pathways operating through growth factor receptors.

5 Claims, No Drawings

PYRROLOTRIAZINE COMPOUNDS

This application claims the benefit of U.S Provisional Application No. 60/584,768, filed Jul. 1, 2004, incorporated herein by reference in its entirety.

FIELD OF THE INVENTION

This invention relates to compounds that inhibit the tyrosine kinase activity of growth factor receptors such as HER1, HER2, HER4, VEGFR-2, FGFR-1, and PDGFR thereby making them useful as anti-cancer agents. The compounds are also useful in the treatment of diseases, other than cancer, which are associated with signal transduction pathways operating through these growth factor receptors.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

Other RTKs such as VEGFR-2 are associated with the proliferation of endothelial cells as well as tumor cells. Disruption of this pathway would have an antiproliferative effect and a therapeutic effect on disorders related to vasculogenesis or angiogenesis.

DETAILED DESCRIPTION OF THE INVENTION

The present invention provides for compounds of formula I, pharmaceutical compositions employing such compounds and methods of using such compounds.

In accordance with the present invention, compounds of formula I

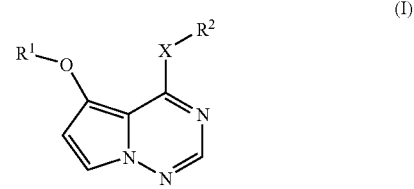

(I)

wherein the symbols have the following meanings and are, for each occurrence, independently selected:

$R^1$ is hydrogen, alkyl, substituted alkyl, cycloalkyl, substituted cycloalkyl, carbocyclic ring, substituted carbocyclic ring, aryl, substituted aryl, heterocyclyl or substituted heterocyclyl; said substituents on the substituted alkyl, cycloalkyl, aryl or heterocyclyl selected from the group consisting of one or more hydrogen, halogen, alkyl, substituted alkyl, aryl, substituted aryl, heterocyclyl, substituted heterocyclyl, —CN, —$N_3$, —$NH_2$, —NH-alkyl, —NH-substituted alkyl, —NH-aryl, —NH-substituted aryl, —NHCOalkyl, imino, alkyl imino, substituted alkyl imino, aryl imino, substituted aryl imino, hydroxyl, alkoxy, substituted alkoxy, aryloxy, substituted aryloxy, carboxy, —CONHalkyl, —CONHsubstituted alkyl, $R^2$ is aryl, substituted aryl, heterocyclyl or substituted heterocyclyl; said substituents on the substituted aryl or substituted heterocyclyl group are selected from the group consisting of one or more hydrogen, halogen, alkyl, substituted alkyl, cycloalkyl, substituted cycloalkyl, alkenyl, substituted alkenyl, alkynyl, substituted alkynyl, —CN, —$N_3$, alkoxy, substituted alkoxy, aryl, substituted aryl, aryloxy, substituted aryloxy, —O-heterocyclyl, —O-substituted heterocyclyl, heterocyclyl, substituted heterocyclyl, —$CF_3$, and —$OCF_3$;

X is a direct bond or —NH—;

or a pharmaceutically acceptable salt, ester, solvate, prodrug or stereoisomer thereof; inhibit the tyrosine kinase activity of growth factor receptors such as HER2.

A further embodiment of the invention is illustrated by a compound of Formula I, or a pharmaceutically acceptable salt, ester, solvate, prodrug or stereoisomer thereof, wherein $R^1$ is cycloalkyl or substituted cycloalkyl, said substituents on the substituted cycloalkyl selected from the group consisting of one or more —OH, —$NH_2$, —NHCN, =O, —NHalkylSO$_2$alkyl, —NHalkylarylCO$_2$alkyl, —NHalkylarylCO$_2$H, —NHalkylCO$_2$H, —NHarylalkylCO$_2$H, —NHalkylarylSO$_2$NHCOalkyl, —NHalkylaryl-NHalkylarylSO$_2$NHCOalky, —NHalkylarylCONHSO$_2$alkyl and —NHCOalkylamino;

R₂ is aryl, substituted aryl, heterocyclyl or substituted heterocyclyl, said substituents on the substituted aryl or heterocyclyl selected from the group consisting of one or more hydrogen, halogen, alkylaryl or substituted alkylaryl; and X is —NH—.

A further embodiment of the invention is illustrated by a compound of Formula I, or a pharmaceutically acceptable salt, ester, solvate, prodrug or stereoisomer thereof, wherein $R^1$ is cyclohexyl or substituted cyclohexyl, said substituents on the substituted cycloalkyl selected from the group consisting of one or more —OH, —NH₂, —NHCN, =O, —NHalkylSO₂alkyl, —NHalkylarylCO₂alkyl, —NHalkylarylCO₂H, —NHalkylCO₂H, —NHarylalkylCO₂H, —NHalkylarylSO₂NHCOalkyl, —NHalkylaryl-NHalkylarylSO₂NHCOalky, —NHalkylarylCONHSO₂alkyl and —NHCOalkylamino.

A further embodiment of the invention is illustrated by a compound of Formula I, or a pharmaceutically acceptable salt, ester, solvate, prodrug or stereoisomer thereof, wherein $R^1$ is heterocyclyl or substituted heterocyclyl.

In a further embodiment of the invention, when $R^1$ is heterocyclyl or substituted heterocyclyl, the heterocyclyl group is selected from the group consisting of thiopyran, oxotetrahydrothiopyran, dioxotetrahydrothiopyran, 1-imino-1-oxo tetrahydrothiopyran, 1-methylimino-1-oxotetrahydrothiopyran, azetidin-COalkyl and piperidin-COalkylamino.

In a further embodiment of the invention, $R^1$ is —CONHalkyl or CONHalkyl.

Illustrative compounds of the invention include the following:

(1,4-cis)-4-(4-(1-(3-Fluorobenzyl)-1H-indazol-5-ylamino)pyrrolo[1,2-f][1,2,4]triazin-5-yloxy)cyclohexanol;

1-(3-Fluorobenzyl)-N-(5-((1,4-cis)-4-aminocyclohexyloxy)H-pyrrolo[1,2-b]pyridazin-4-yl)-1H-indazol-5-amine;

1-(3-Fluorobenzyl)-N-(5-((1,4-trans)-4-aminocyclohexyloxy)H-pyrrolo[1,2-b]pyridazin-4-yl)-1H-indazol-5-amine;

5-((1,4-cis)-4-Aminocyclohexyloxy)-N-(3-chloro-4-fluorophenyl)pyrrolo[1,2-f][1,2,4]triazin-4-amine;

N-(1-(3-Fluorobenzyl)-1H-indazol-5-yl)-5-((1,4-cis)-4-(2-(methylsulfonyl)-ethylamino)cyclohexyloxy)pyrrolo[1,2-f][1,2,4]triazin-4-amine;

N-(1-(3-Fluorobenzyl)-1H-indazol-5-yl)-5-((1,4-trans)-4-(2-(methylsulfonyl)ethylamino)cyclohexyloxy)pyrrolo[1,2-f][1,2,4]triazin-4-amine;

4-(((1,4-trans)-4-(4-(1-(3-Fluorobenzyl)-1H-indazol-5-ylamino)pyrrolo[1,2-f][1,2,4]triazin-5-yloxy)cyclohexylamino)methyl)benzoic acid;

4-(((1,4-cis)-4-(4-(1-(3-Fluorobenzyl)-1H-indazol-5-ylamino)pyrrolo[1,2-f][1,2,4]triazin-5-yloxy)cyclohexylamino)methyl)benzoic acid;

4-(((1,4-trans)-4-(4-(3-chloro-4-(pyridin-2-ylmethoxy)phenylamino)pyrrolo-[1,2-f][1,2,4]triazin-5-yloxy)cyclohexylamino)methyl)benzoic acid;

4-(((1,4-cis)-4-(4-(3-chloro-4-(pyridin-2-ylmethoxy)phenylamino)pyrrolo-[1,2-f][1,2,4]triazin-5-yloxy)cyclohexylamino)methyl)benzoic acid;

1-(4-(4-(1-(3-fluorobenzyl)-1H-indazol-5-ylamino)pyrrolo[1,2-f][1,2,4]triazin-5-yloxy)cyclohexylamino)cyclopropanecarboxylic acid, isomer A and B;

4-(((1,4-trans)-4-(4-(1-(3-Fluorobenzyl)-1H-indazol-5-ylamino)pyrrolo[1,2-f][1,2,4]triazin-5-yloxy)cyclohexylamino)methyl)-N-(methylsulfonyl)benzamide;

N-((1,4-cis)-4-(4-(1-(3-Fluorobenzyl)-1H-indazol-5-ylamino)pyrrolo[1,2-f][1,2,4]triazin-5-yloxy)cyclohexyl)-2-aminoacetamide;

N-((1,4-trans)-4-(4-(1-(3-Fluorobenzyl)-1H-indazol-5-ylamino)pyrrolo[1,2-f][1,2,4]triazin-5-yloxy)cyclohexyl)-2-aminoacetamide;

1-(4-(4-(1-(3-Fluorobenzyl)-1H-indazol-5-ylamino)pyrrolo[1,2-f][1,2,4]triazin-5-yloxy)piperidin-1-yl)-2-aminoethanone;

(1R,2R,5S)- and (1S,2S,5R)-5-(4-(1-(3-fluorobenzyl)-1H-indazol-5-ylamino)pyrrolo[1,2-f][1,2,4]triazin-5-yloxy)-2-aminocyclohexanol;

(1R,2R,5R) and (1S,2S,5S)-5-(4-(1-(3-fluorobenzyl)-1H-indazol-5-ylamino)pyrrolo[1,2-f][1,2,4]triazin-5-yloxy)-2-aminocyclohexanol;

or a pharmaceutically acceptable salt, ester, solvate, prodrug or stereoisomer thereof.

Compounds of the instant invention exhibit IC₅₀ values of less than 5 μM in one or more of HER1, HER2 and HER4 assays.

Also included within the scope of the invention is a pharmaceutical composition which comprises at least one compound of formula I as described above and a pharmaceutically acceptable carrier.

Also included is a method for treating proliferative diseases, comprising administering to a mammal in need thereof, a therapeutically effective amount of at least one compound of formula I.

Also included is a method for treating or preventing cancer, comprising administering to a mammal in need thereof, a therapeutically effective amount of at least one compound of formula I.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, substituted alkylamino, cycloalkylamino, substituted cycloalkylamino, arylamino, substituted arylamino, aralkylamino, substituted aralkyamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO₂NH₂, substituted sulfonamido, nitro, cyano, carboxy, carbamyl, e.g. CONH₂, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolinyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclyls, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention includes all the possible stereoisomers and their mixtures. Paricularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:
- a) *Design of Prodrugs*, edited by H. Bundgaard, (Elsevier, 1985) and *Methods in Enzymology*, Vol. 112, p. 309–396, edited by K. Widder, et al. (Acamedic Press, 1985);
- b) *A Textbook of Drug Design and Development*, edited by Krosgaard-Larsen and H. Bundgaard, Chapter 5, "Design and Application of Prodrugs," by H. Bundgaard, p. 113–191 (1991);
- c) H. Bundgaard, Advanced Drug Delivery Reviews, 8, 1–38 (1992);

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, pyrrolotriazines such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, esophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of noncancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a mammalian species such as a human being.

According to a further feature of the invention there is provided a method for producing an antiproliferative effect in a mammalian species, such as a human being, in need of such treatment which comprises administering to said animal an effective amount of a compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agens such as Taxol, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as antiangiogenic agents. See the following documents and references cited therein: Schlessinger J. , "Cell signaling by receptor tyrosine kinases", *Cell* 103(2), p. 211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260–265 (2001).

The antiproliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be: surgery, radiotherapy or chemotherapy. Such chemotherapy may cover three main categories of therapeutic agent:
(i) antiangiogenic agents that work by different mechanisms from those defined hereinbefore (for example, linomide, inhibitors of integrin αvβ3 function, angiostatin, razoxane);
(ii) cytostatic agents such as antiestrogens (for example, tamoxifen, toremifene, raloxifene, droloxifene, iodoxifene), progestogens (for example megestrol acetate), aromatase inhibitors (for example anastrozole, letrozole, borazole, exemestane), antihormones, antiprogestogens, antiandrogens (for example flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and
(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors; biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:
carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
tumors of mesenchymal origin, including fibrosarcoma and rhabdomyosarcoma;
tumors of the central and peripheral nervous system, including astrocytoma, neuroblastoma, glioma and schwannomas; and
other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders, suspensions and the like. The compounds may be administered in a dosage range of about 0.05 to 300 mg/kg/day, preferably less than 200 mg/kg/day, in a single dose or in 2 to 4 divided doses.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 µM ATP, and 4 µCi/ml [$\gamma$-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with $IC_{50}$ values between 0.001 and 25 µM. Preferred compounds have $IC_{50}$ values between 0.001–5.0 µM. More preferred compounds have $IC_{50}$ values between 0.001–1.0 µM. Most preferred compounds have $IC_{50}$ values between 0.001–0.1 µM.

A HERG potassium channel assay may be used to screen compounds for HERG activity (see Caballero R, et al., *Direct Effects of Candesartan and Eprosartan on Human Cloned Potassium Channels Involved in Cardiac Repolarization*, Molecular Pharmacology, Vol. 59, No. 4, pp. 825–36, 2001). Accordingly, preferred compounds have lower HERG assay activity.

Methods of Preparation

Certain compounds of formula I may generally be prepared according to the following schemes and the knowledge of one skilled in the art. Supplemental preparation information may also be found in co-pending U.S. patent application Ser. No. 09/573,829 filed May 18, 2000 and international applications published under the Patent Cooperation Treaty (PCT), International Publication Number WO 00/71129 and WO 03/042172, all of which are incorporated by reference herein.

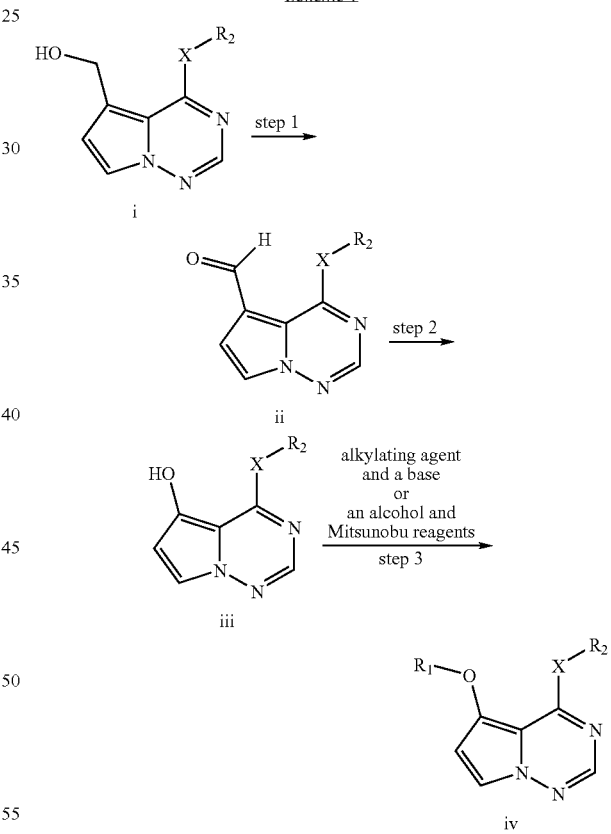

Scheme 1

Step 1: The first step of Scheme 1 involves oxidation of the 5-hydroxymethyl pyrrolotriazine i (Ref. WO 03/042172 A2) to the aldehyde ii. This can be accomplished with a variety of oxidizing agents, e.g., manganese dioxide.

Step 2: The aldehyde ii undergoes a Bayer-Villiger rearrangement (review: G. R. Krow, Organic Reactions, 1993, 43, 251) with concomitant hydrolysis of the formate ester intermediate on treatment with the appropriate oxidant to give iii.

Step 3: Treatment of iii with a base such a NaH in an anhydrous solvent such as DMF with the appropriate alkylating agent (e.g., alkyl halides, dialkyl sulfates, alkyl triflates) gives, after the removal of any protecting groups that were on the alkylating agent and/or after the modification or further elaboration of functional groups that were on this residue, the final product, iv. Alternatively, the Mitsunobu reaction (review: D. L. Hughes, Organic Reactions, 1992, 42, 335) of iii with the appropriate alcohol gives, after the removal of any protecting groups that were on the alkylating agent and/or after the modification or further elaboration of functional groups that were on this residue, the final product, iv. Other variants of the Mitsunobu reaction can also be used for this, e.g., T. Tsunoda et al., Tetrahedron Lett., 1995, 36, 2529.

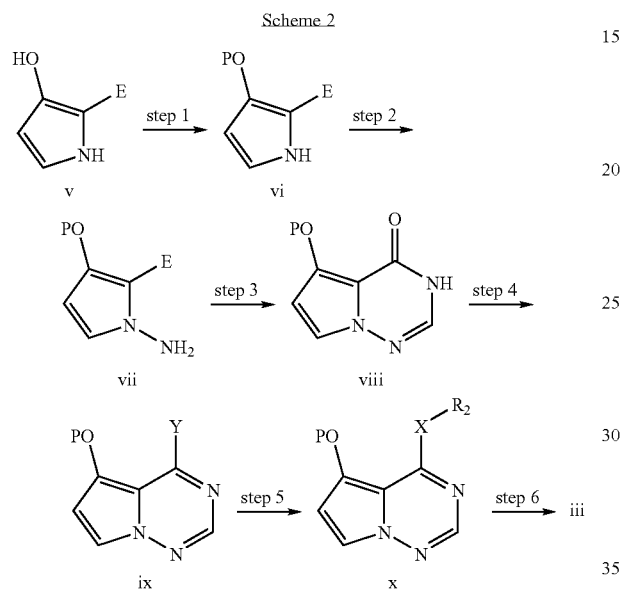

wherein E is an ester group and PO is a protected hydroxy group and Y is a halogen Step 1: The first step of Scheme 1, involves protection of the 3-hydroxy group of a 3-hydroxy-1H-pyrrole-2-carboxylic acid ester v (T. Momose et al., Chem. Pharm. Bull., 1978, 26, 2224) to give vi. Various protected alcohol groups can be used for this, e.g., arylsulfonates or substituted benzyl ethers. These protecting groups are attached by treatment of v with a base such as diisopropylethylamine in an anhydrous solvent such as DCM followed by an arylsulfonyl halide, or an arylsulfonic anhydride or by treatment of v with a base such as NaH in an anhydrous solvent such as THF or DMF followed by a benzyl halide or a substituted benzyl halide.

Step 2: This involves treating the pyrrole vi with a base such as potassium t-butoxide or sodium hydride in an anhydrous solvent such as THF or DMF followed by an aminating reagent, such as O-(2,4-dinitro-phenyl)-hydroxylamine (T. Sheradsky, J. Heterocyclic Chem., 1967, 4, 413) or chloramines (I. P. Sword, J. Chem. Soc. C, 1971, 820) to give the 1-aminopyrrole vii.

Step 3: The 1-aminopyrrole vii is heated with excess formamide to give the pyrrolotriazinone viii.

Step 4: Compound viii is converted to a 4-halo-pyrrolotriazine ix by heating with the appropriate phosphorus oxyhalide, e.g., the 4-chloro-pyrrolotriazine ix is obtained by heating viii with phosphorus oxychloride.

Step 5: Treatment of viii with the appropriate amine, alcohol or thiol in the presence of a base such as NaHCO$_3$ or triethylamine in a solvent such as acetonitrile affords x. Alternatively, heating a mixture of viii and the appropriate amine in a alcoholic solvent or a solvent mixture such as that of an alcohol and 1,2-dichloroethane affords the acid (HX) salt of x.

Step 6: Standard removal of the protecting group of vi gives the 5-hydroxypyrroltriazine iii which can be converted to the final product iv as was outlined in Scheme 1.

In addition, other compounds of formula I may be prepared using procedures generally known to those skilled in the art. In particular, the following examples provide additional methods for the preparation of the compounds of this invention.

Unless otherwise indicated, "HPLC Ret. Time" is the HPLC retention time that was obtained under the following conditions: column type and length, gradient time (unless otherwise indicated, all gradients started with 100% solvent A and ended with 100% solvent B; for Phenomenex Primeshpere columns, solvent A was a mixture of CH$_3$CN:water:5.0 M NH$_4$OAc=1:9:0.005 and solvent B was CH$_3$CN:water:5.0 M NH$_4$OAc=9:1:0.005; for YMC xterra columns, solvent A was a mixture of MeOH:water:TFA=1:9:0.01 and solvent B was MeOH:water:TFA=9:1:0.01), flow rate (ml/min). UV detection was always conducted at 220 nM.

EXAMPLE 1

4-(1-(3-Fluorobenzyl)-1H-indazol-5-ylamino)pyrrolo[1,2-f][1,2,4]triazin-5-ol

Method A

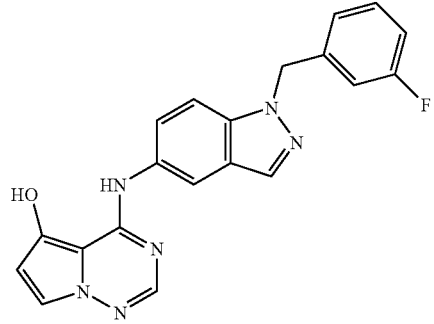

1A. Preparation of 4-(1-(3-Fluorobenzyl)-1H-indazol-5-ylamino)pyrrolo[1,2-f][1,2,4]triazine-5-carbaldehyde

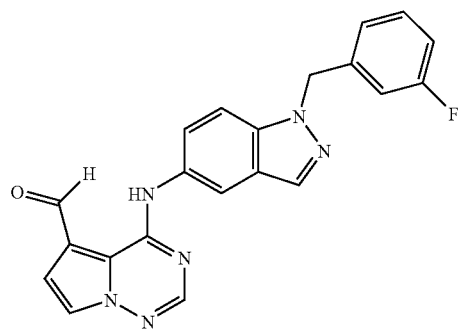

A mixture of MnO$_2$ (2.78 gm, 32.2 mmole), (4-(1-(3-fluorobenzyl)-1H-indazol-5-ylamino)pyrrolo[1,2-f][1,2,4]

triazin-5-yl)methanol (Ref. WO 2003043172 A2) (499 mg, 1.28 mmole) in dry DCM (24 mL) under $N_2$ was heated at 30° C. for 1.5 hr. The reaction was filtered through a short celite pad to give the product (482 mg, 97%): $^1$H NMR (CDCl$_3$): 5.59 (s, 2H), 6.86 (m, 1H), 6.96 (m, 2H), 7.16 (m, 1H), 6.28 (m, 1H), 7.33 (m, 1H), 7.53 (m, 1H) 7.67(m, 1H), 8.07 (s, 1H), 8.17 (s, 1H), 8.47 (m, 1H), 9.75 (s, 1H); MS: 387 (M+H)$^+$; HPLC Ret Time: 2.57 min (YMC Xterra S7 3.0×50 mm column, 3 min gradient, 5 mL/min).

1B. 4-(1-(3-Fluorobenzyl)-1H-indazol-5-ylamino) pyrrolo[1,2-f][1,2,4]triazin-5-ol Solid m-chloroperbenzoic acid (64 mg, 70%, 0.26 mmole) was added to an ice-cooled solution of 1A (39 mg, 0.10 mmole) in DCM (1.5 mL). A solution of TFA (0.023 mL, 0.20 mmole) in DCM (1 mL) was added dropwise and the reaction was left stirring for 5 hr. It was diluted with DCM and washed with a 10% aq. solution of NaHSO$_3$, saturated aq. NaHCO$_3$, dried (Na$_2$SO$_4$) and the solvents removed. Radial chromatography on silica gel (step gradient elution with 0 to 3% of a methanolic solution of NH$_3$ in DCM) afforded the product (14 mg, 37%): $^1$H NMR (DMSO-D$_6$): 5.69 (s, 2H), 6.14 (m, 1H), 7.02 (m, 1H), 7.08 (m, 1H), 7.35 (m, 1H), 7.42 (m, 1H), 7.59 (m, 1H), 7.71 (m, 2H), 8.13 (s, 1H), 8.30 (m, 1H), 8.45 (s, 1H); MS: 375(M+ H)$^+$; HPLC Ret Time: 1.13 min (YMC Xterra S7 3.0×50 mm column, 2 min gradient, 5 mL/min).

Method B

1C. Preparation of Methyl 3-(tosyloxy)-1H-pyrrole-2-carboxylate

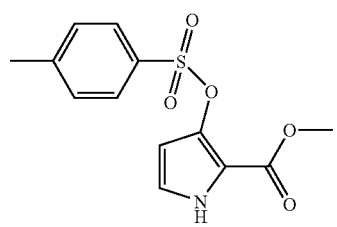

Diisopropylethylamine (7.1 mL, 40.7 mmole) and then a solution of TsCl (6.46 gm, 33.9 mole) in dry DCM (20 mL) were added to an ice-cooled solution of methyl 3-hydroxy-1H-pyrrole-2-carboxylate (4.78 gm; 33.9 mmole) in dry DCM (80 mL) under a dry N$_2$ atmosphere. After 2 hr, the reaction was removed from the bath and allowed to warm to RT. After 2 hr, this was washed with water, dried (Na$_2$SO$_4$), and the solvents removed to leave methyl 3-(tosyloxy)-1H-pyrrole-2-carboxylate (10 gm) as a solid. $^1$H NMR (CDCl$_3$): 2.39 (s, 3H), 3.64 (s, 3H), 6.06 (m, 1H), 6.75 (m, 1H), 7.26 (m, 2H), 7.71 (m, 2H); MS: 311(M+H)$^+$; HPLC Ret Time: 1.28 min (YMC Xterra S7 3.0×50 mm column, 2 min gradient, 5 mL/min).

1D. Preparation of Methyl 1-amino-3-(tosyloxy)-1H-pyrrole-2-carboxylate

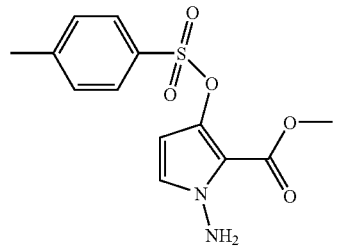

Solid methyl 3-(tosyloxy)-1H-pyrrole-2-carboxylate (1.33 μm, 4.50 mmole) was added in portions to an ice-cooled suspension of NaH (60% in mineral oil, 234 mg, 5.85 mmole) in dry DMF (15 mL) under a dry N$_2$ atmosphere. Upon completion of the addition, the reaction was removed from the bath and left stirring at RT. After 1 hr, a solution of NH$_2$Cl (59 mL; 0.1 M in Et$_2$O prepared according to J. Chem. Soc. C, 1971, 824; 5.85 mmole) was added and the reaction was left stirring for 1.3 hr. It was then cooled to −5° C. and an aqueous solution of Na$_2$S$_2$O$_4$ (20 mL, 1.0 M) was slowly added over 5 min. Water (60 mL) was added and the bath was removed. After 10 min, this was extracted with EtOAc (2×200 mL) and the organic extracts were washed with brine and dried (Na$_2$SO$_4$). Removal of the solvents followed by flash chromatography on silica gel using step gradient elution (hexane:EtOAc from 100:0 to 70:30) afforded the title compound (1.22 gm, 88% yield) as a solid. $^1$H NMR (CDCl$_3$): 2.39 (s, 2H), 3.62 (s, 3H), 5.44 (s, 2H), 5.76 (m, 1H), 6.73 (m, 1H), 7.26 (m, 2H), 7.66 (m, 2H); MS: 311 (M+H)$^+$; HPLC Ret Time: 1.28 min (YMC Xterra S7 3.0×50 mm column, 2 min gradient, 5 mL/min).

1E. Preparation of 4-Oxo-3,4-dihydropyrrolo[1,2-f][1,2,4]triazin-5-yl 4-methylbenzenesulfonate

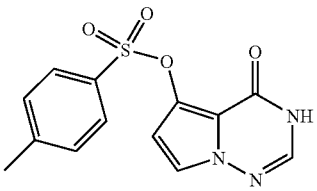

A mixture of methyl 1-amino-3-(tosyloxy)-1H-pyrrole-2-carboxylate (13.65 gm, 44.0 mmole) and phosphoric acid (862 mg, 8.8 mmole) in formamide (44 mL) was heated at 120° C. under a dry N$_2$ atmosphere for 15 hr. DCM (600 mL) was added and the reaction was extracted with saturated aqueous NaHCO$_3$ solution (200 mL) and then water (200 mL). The aqueous extracts were back extracted with DCM and the combined organic phases were washed with brine and dried (Na$_2$SO$_4$). This was concentrated to about 150 mL and pure product separated as a precipitate that was collected by filtration (6.19 μm). Removal of the solvent from the mother liquor followed by crystallization from EtOAc/ hexane afforded an additional 2.44 of pure product. A further 1.49 gm of pure product (total yield: 10.12 gm, 75%) was obtained by flash chromatography of the final mother liquor on silica gel using step gradient elution with mixtures of DCM:MeOH=99.8:0.2 to 99.3:0.7. $^1$H NMR (CDCl$_3$): 2.41 (s, 3H), 6.28 (m, 1H), 7.23 (m, 1H), 7.29 (m, 1H), 7.57 (s, 1H), 7.80 (m, 2H); MS: 306 (M+H)$^+$; HPLC Ret Time: 1.19 min (YMC Xterra S7 3.0×50 mm column, 2 min gradient, 5 mL/min).

1F. Preparation of 4-Chloropyrrolo[1,2-f][1,2,4]triazin-5-yl 4-methylbenzenesulfonate

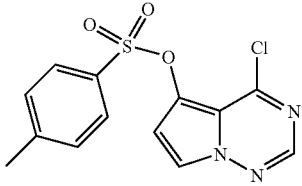

POCl$_3$ (2.32 mL, 15 mmole) was added to a mixture of 4-oxo-3,4-dihydropyrrolo[1,2-f][1,2,4]triazin-5-yl 4-methylbenzenesulfonate (3.05 gm, 10 mmole) and diisopropylethylamine (1.74 mL, 10 mmole) in dry toluene (40 mL) under a dry N$_2$ atmosphere. This was heated at reflux for 15 hr and then allowed to cool to RT. A saturated aqueous solution of NaHCO3 was added and this reaction was left stirring for 10 min. This was then diluted with DCM and the organic phase was separated, washed with brine and dried (Na$_2$SO$_4$). Flash chromatography on silica gel with DCM as eluent afforded the product as a yellow solid (2.78 gm, 86%).

$^1$H NMR (CDCl$_3$): 2.46 (s, 3H), 6.77 (m, 1H), 7.34 (m, 1H), 7.69 (m, 1H), 7.77 (s, 1H), 8.13 (m, 2H); MS: 324 (M+H)$^+$; HPLC Ret Time: 1.53 min (YMC Xterra S7 3.0×50 mm column, 2 min gradient, 5 mL/min).

1G. Preparation of 4-(1-(3-Fluorobenzyl)-1H-indazol-5-ylamino)pyrrolo[1,2-f][1,2,4]triazin-5-ol A mixture of 4-chloro-1H-pyrrolo[1,2-b]pyridazin-5-yl 4-methyl-benzenesulfonate (7.01 gm, 21.67 mmole) and 1-(3-fluorobenzyl)-1H-indazol-5-amine (5.48 gm, 22.8 mmole) in dry 1,2-dichloroethane (44 mL) and dry n-butanol (22 mL) was heated at 90° C. for 50 min. After removal of the solvents, the residual solid was suspended in dry THF (225 mL) and the reaction was cooled in an ice bath. NaOMe (18.7 mL, 25 wt % in MeOH, about 87 mmole) was added. After 30 min, a saturated aqueous solution of NH$_4$Cl (400 mL) was added and the reaction was left stirring for 5 min before being extracted with EtOAc. The extracts were washed with brine, dried (Na$_2$SO$_4$), and concentrated. The product precipitated from the concentrate and was collected by filtration (5.31 gm, 92%).

EXAMPLE 2

N-(1-(3-Fluorobenzyl)-1H-indazol-5-yl)-5-methoxy-pyrrolo[1,2-f][1,2,4]triazin-4-amine

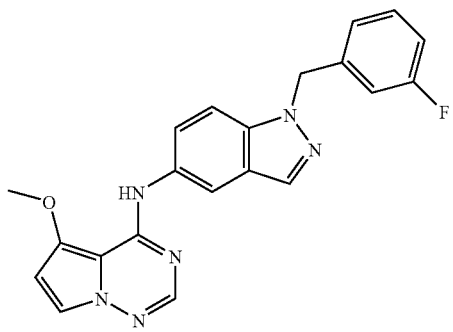

A solution of 4-(1-(3-fluorobenzyl)-1H-indazol-5-ylamino)H-pyrrolo[1,2-b]pyridazin-5-ol (39.1 mg, 0.104 mmole) in dry THF (3 mL) was treated with NaH (2.76 mg, 0.115 mmole) and stirred at 23° C. for 0.25 hr before adding MeI (7.1 μL, 0.115 μmole). After 16 hr, the mixture was diluted with EtOAc and washed with brine. The organic phase was dried (MgSO$_4$) and concentrated in vacuo. The crude material was purified by flash chromatography on silica gel with mixtures of 10 to 20% of EtOAc in DCM to give the product (5 mg, 12%): $^1$H NMR (CD$_3$OD): 3.9 (s, 3H), 5.57 (s, 2H), 6.31 (d, J=3.05 Hz, 1H), 6.88 (m, 1H), 6.91 (m, 2H), 7.22 (m, 1H), 7.29 (d, J=2.03 Hz, 1H), 7.45 (m, 2H), 7.53 (s, 1H), 7.99 (s, 1H), 8.05 (m, 1H), MS: 389 (M+H)$^+$; HPLC Ret Time: 1.86 min (Phenomenex Primesphere 5μ C4, 4.6×30 mm column, 2 min gradient, 4 mL/min).

EXAMPLE 3

(1,4-cis)-4-(4-(1-(3-Fluorobenzyl)-1H-indazol-5-ylamino)pyrrolo[1,2-f][1,2,4]triazin-5-yloxy)cyclohexanol

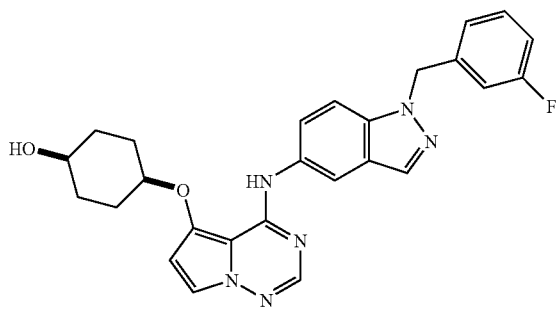

Diethyl azodicarboxylate (70 mg, 0.4 mmole) was added to a solution of 1 (50 mg, 0.134 mmole), trans-cyclohexane-1,4-diol (47 mg, 0.4 mmole) and triphenylphosphine (105 mg, 0.4 mmole) in dry THF. After stirring at RT for 20 hr, the solvent was evaporated and the residue was flash chromatographed on a silica gel column that was eluting with a mixture of ethyl acetate:hexane=1:1 to give the product (31 mg, 49%): MS: 473 (M+H)+; HPLC Ret Time: 1.92 min (Phenomenex Primesphere 5μ C4, 4.6×30 mm column, 2 min gradient, 4 mL/min). A sample was dissolved in THF and treated with one equivalent of an 0.8 N solution of HCl in dioxane. Removal of the solvent left the hydrochloride salt: $^1$H NMR (DMSO-D$_6$): 1.76–1.45 (m, 6H), 2.06–1.94 (m, 2H), 3.63 (m, 1H), 4.49 (m, 1H), 5.70 (s, 2H), 6.52 (d, 1H), 7.07–6.98 (m, 2H), 7.09 (dt, 1H), 7.4–7.3 (m, 1H), 7.53 (dd, 1H), 7.59 (d, 1H), 7.76 (d, 1H), 7.84 (s, 1H), 8.16 (s, 1H), 8.39 (s, 1H). MS: 473 (M+H)+.

EXAMPLE 4

4-(4-(1-(3-Fluorobenzyl)-1H-indazol-5-ylamino) pyrrolo[1,2-f][1,2,4]triazin-5-yloxy)cyclohexanone

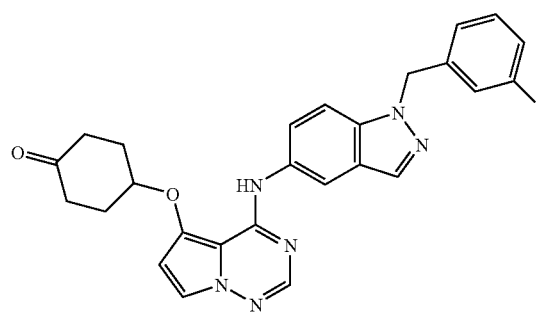

A solution of 1 (500 mg, 1.34 mmole), 1-hydroxy-4-cyclohexanone ethylene ketal; (635 mg, 4.0 mmole) and triphenylphosphine (1.05 gm, 4.0 mmole) in THF was treated dropwise with diethyl azodicarboxylate (695 mg, 4.0 mmole). After stirring at RT for 20 hr, the solvent was evaporated. The residue was applied onto a pad of SCX silica gel (6.0 gm, Silicycle) and eluted with MeOH followed by a 2N solution of NH$_3$ in MeOH. The fractions that contained the desired material were combined and the solvent removed. A solution of this residue and p-toluenesulfonic acid (100 mg) in 90% aqueous acetone (25 ml) was heated at reflux for 20 hr. After cooling to RT, this was made slightly basic with NaHCO$_3$ and the solvent was removed. The residue was taken up in EtOAc, washed with water dried (MgSO4) and the solvent removed. Flash chromatography on silica gel eluting with EtOAc in hexane (1:1) gave the product (422 mg, 67.0%): MS: 471 (M+H)+; HPLC Ret Time: 1.81 min (Phenomenex Primesphere 51 C4, 4.6×30 mm column, 2 min gradient, 4 mL/min). Treatment of a sample with one equivalent of a 0.8N solution of HCl in dioxane followed by removal of the solvent afforded the hydrochloride salt: $^1$H NMR (DMSO-D6): 2.59–2.10 (m, 8H), 4.86 (t, 1H), 5.72 (s, 2H), 6.7 (d, 1H), 7.15–6.90 (m, 3H), 7.4–7.3 (m, 1H), 7.55–7.46 (m, 1H), 7.8–7.7 (m, 3H), 8.27–8.14 (m, 2H), 9.0 (broad s, 1H).

EXAMPLE 5

1-(3-Fluorobenzyl)-N-(5-((1,4-cis)-4-aminocyclohexyloxy)H-pyrrolo[1,2-b]pyridazin-4-yl)-1H-indazol-5-amine

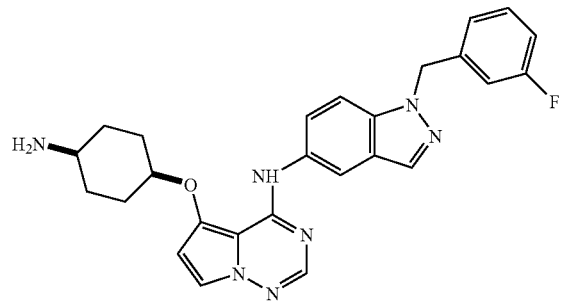

5A. Preparation of tert-Butyl (1,4-cis)-4-(4-(1-(3-fluorobenzyl)-1H-indazol-5-ylamino)pyrrolo[1,2-f][1,2,4]triazin-5-yloxy)cyclohexylcarbamate

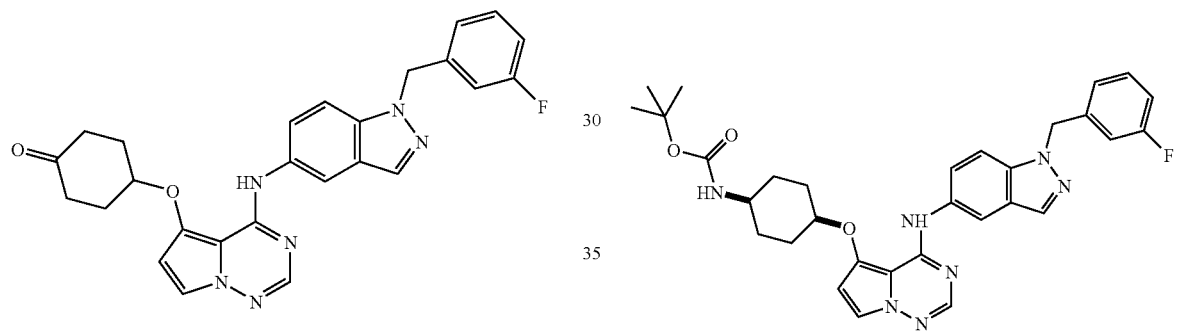

Azodicarboxylic acid bis(dimethylamide) (184 mg, 1.07 mmole) was added to a mixture of 1 (200 mg, 0.53 mmole), tert-butyl(1,4-trans)-4-hydroxycyclohexyl-carbamate (173 mg, 0.805 mmole), and tri-n-butylphosphine (0.264 mL, 1.07 mmole) in dry toluene (4 m-tL) at RT under a dry N$_2$ atmosphere. After 1 hr, this was heated at 60° C. for 1.7 hr. On cooling to RT, the reaction was diluted with DCM, filtered, and the filtrate was applied onto the 2 mm silica gel plate of a radial chromatotron. Elution with a mixture of EtOAc:hexane=2:3 afforded tert-butyl(1,4-trans)4-(4-(1-(3-fluorobenzyl)-1H-indazol-5-ylamino)H-pyrrolo[1,2-b]pyridazin-5-yloxy)cyclohexylcarbamate as an oil (167 mg, 55%). MS: 572 (M+H)+; HPLC Ret Time: 2.64 min (YMC Xterra S5 4.6×50 mm column, 3 min gradient, 4 mL/min).

5B. Preparation of 1-(3-Fluorobenzyl)-N-(5-((1,4-cis)-4-aminocyclohexyloxy)H-pyrrolo[1,2-b]pyridazin-4-yl)-1H-indazol-5-amnine 5A (167 mg) was treated with a mixture of dry DCM (2 mL) and TFA (2 mL) at RT for 0.5 hr. After removal of the solvents, the residue was taken up in DCM, washed with a 1:1 mixture of a saturated aqueous solution of Na$_2$CO$_3$ and water, and then dried (Na$_2$SO$_4$). Removal of the solvents left the product as a glass (128 mg, 93%): $^1$H NMR (CDCl$_3$): 1.70 (m, 8H), 2.17 (m, 2H), 2.88 (m, 1H), 4.47 (m, 1H), 5.56 (s, 1H), 6.19 (s, 1H), 6.83 (m, 1H), 6.94 (m,2H), 7.25 (m, 1H), 7.32 (m, 2H), 7.52 (m, 1H), 7.82 (s, 1H), 7.04 (s, 1H), 7.15 (s, 1H), 8.30 (s, 1H); MS: 472 (M+H)+; HPLC Ret Time: 1.82 min (YMC Xterra S5 4.6×50 mm column, 3 min gradient, 4 mL/min).

EXAMPLE 6

1-(3-Fluorobenzyl)-N-(5-((1,4-trans)-4-aminocyclohexyloxy)H-pyrrolo[1,2-b]pyridazin-4-yl)-1H-indazol-5-amine

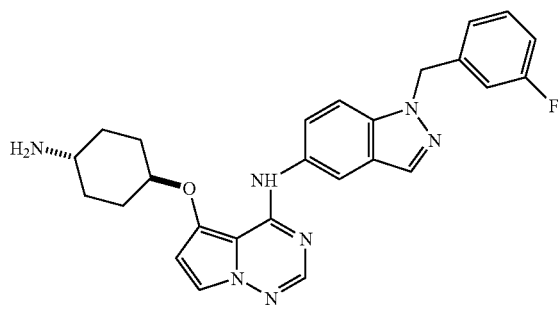

Compound 6 was prepared from 1 and tert-butyl (1,4-cis)-4-hydroxycyclohexyl-carbamate in the same manner as Example 5 and exhibited: MS: 472 (M+H)+; HPLC Ret Time: 1.76 min (YMC Xterra S5 4.6×50 mm column, 3 min gradient, 4 mL/min).

EXAMPLE 7

5-((1,4-cis)-4-Aminocyclohexyloxy)-N-(3-chloro-4-fluorophenyl)pyrrolo[1,2-f][1,2,4]triazin-4-amine

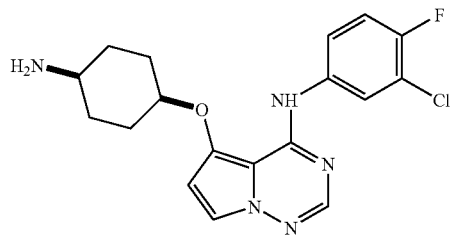

7A. Preparation of 4-(3-Chloro-4-fluorophenylamino)pyrrolo[1,2-f][1,2,4]triazin-5-ol

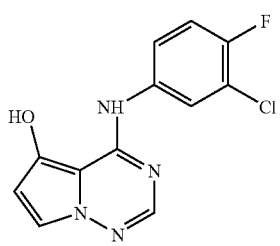

Compound 7A was prepared from 1F and 3-chloro-4-fluoroaniline in the same manner as 1G and exhibited: MS: 279 (M+H)+; HPLC Ret Time: 1.72 min (Phenomenex Primesphere 5μ C4, 4.6×30 mm column, 2 min gradient, 4 mL/min).

7B: Preparation of 5-((1,4-cis)-4-Aminocyclohexyloxy)-N-(3-chloro-4-fluorophenyl)pyrrolo[1,2-f][1,2,4]triazin-4-amine Compound 7 was prepared from 7A and tert-butyl (1,4-trans)-4-hydroxycyclohexylcarbamate in the same manner as Example 5 and exhibited: MS: 376 (M+H)+; HPLC Ret Time: 1.36 min (YMC Combiscreen S5 C8, 4.6×30 mm column, CH3CN:water:TFA=1:9:0.005 to CH3CN:water:TFA=9:1:0.005, 2 min gradient, 4 mL/min).

EXAMPLE 8

5-((1,4-cis)-4-aminocyclohexyloxy)-N-(3-chloro-4-(pyridin-2-ylmethoxy)phenyl)pyrrolo[1,2-f][1,2,4]triazin-4-amine

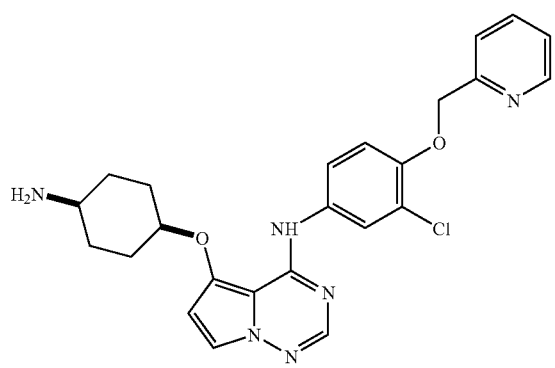

8A. Preparation of 4-(3-Chloro-4-(pyridin-2-ylmethoxy)phenylamino)-pyrrolo[1,2-f][1,2,4]triazin-5-ol

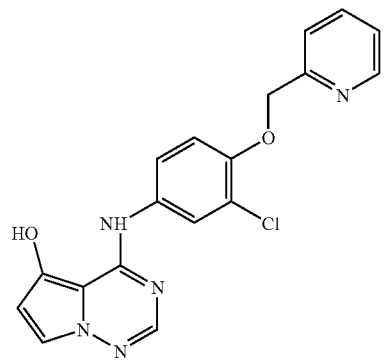

Compound 8A was prepared from 1F and 3-chloro-4-(pyridin-2-ylmethoxy)-benzenamine in the same manner as 1G and exhibited: MS: 368 (M+H)+; HPLC Ret Time: 1.59 min (Phenomenex Primesphere 51 C4, 4.6×30 mm column, 2 min gradient, 4 mL/min).

8B: Preparation of 5-((1,4cis)-4-aminocyclohexyloxy)-N-(3-chloro-4-(pyridin-2-ylmethoxy)phenyl)pyrrolo[1,2-f][1,2,4]triazin-4-amine Compound 8 was prepared from 8A and tert-butyl (1,4-trans)-4-hydroxycyclohexylcarbamate in the same manner as Example 4 and exhibited: MS: 465 (M+H)+; HPLC Ret Time: 1.19 min (Phenomenex Primesphere 5g C4, 4.6×30 mm column, 2 min gradient, 4 mL/min).

EXAMPLE 9

5-((1,4-trans)-4-aminocyclohexyloxy)-N-(3-chloro-4-(pyridin-2-ylmethoxy)phenyl)pyrrolo[1,2-f][1,2,4]triazin-4-amine

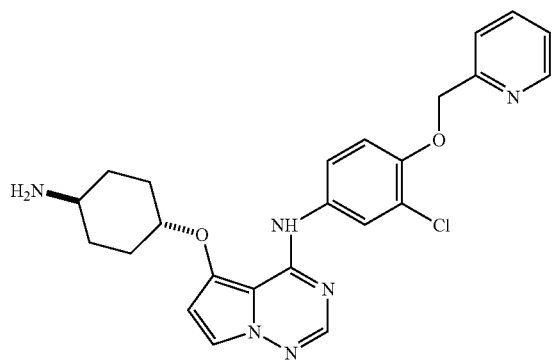

Compound 9 was prepared from 8A and tert-butyl (1,4-cis)-4-hydroxycyclohexyl-carbamate in the same manner as example 6 and exhibited: MS: 465 (M+H)+; HPLC Ret Time: 0.99 min (YMC Xterra S5 3×50 mm column, 2 min gradient, 5 mL/min).

EXAMPLE 10

N-(1-(3-Fluorobenzyl)-1H-indazol-5-yl)-5-((1,4-cis)-4-(2-(methylsulfonyl)-ethylamino)cyclohexyloxy)pyrrolo[1,2-f][1,2,4]triazin-4-amine

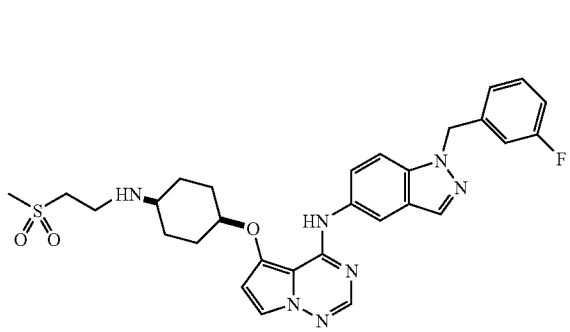

A solution of 5 (50 mg, 0.106 mmole) and methyl vinyl sulfone (21 mg, 0.2 mmole) in MeOH was left stirring at RT for 18 hr. The precipitate was collected and purified by silica gel chromatography with acetonitrile as eluent to give the product (36 mg, 59%): MS: 578 (M+H)+; HPLC Ret Time: 1.81 min (Phenomenex Primesphere 5v C4, 4.6×30 mm column, 2 min gradient, 4 mL/min). Treatment of a sample with one equivalent of a 0.8N solution of HCl in dioxane followed by removal of the solvent afforded the hydrochloride salt: 1H NMR (DMSO-D6): 1.83–1.65 (m, 4H), 2.03–1.90 (m, 2H), 2.35–2.19 (m, 2H), 3.13 (s, 3H), 3.27 (m, 1H), 3.64–3.49 (m, 3H), 4.60 (s, 1H), 5.72 (s, 2H), 6.50 (d, 1H), 7.06–6.97 (m, 2H), 7.11 (dt, 1H), 7.41–7.32 (m, 1H), 7.62–7.56 (m, 2H), 7.73 (d, 1H), 7.86 (s, 1H), 8.17 (s, 1H), 8.23 (s, 1H), 8.45 (d, 1H), 8.94 (broad s, 1H).

EXAMPLE 11

N-(1-(3-Fluorobenzyl)-1H-indazol-5-yl)-5-((1,4-trans)-4-(2-(methylsulfonyl)ethylamino)cyclohexyloxy)pyrrolo[1,2-f][1,2,4]triazin-4-amine

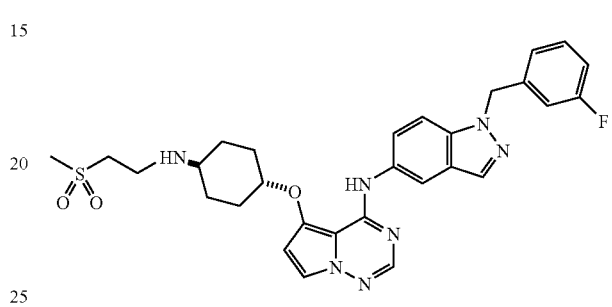

Compound 11 was prepared from 6 and methyl vinyl sulfone in the same manner as Example 10 and exhibited: MS: 578 (M+H)+; HPLC Ret Time: 1.96 min (Phenomenex Primesphere 51 C4, 4.6×30 mm column, 2 min gradient, 4 mL/min).

EXAMPLE 12

N-(1-(3-Fluorobenzyl)-1H-indazol-5-yl)-5-((1,4-cis)-4-(isocyanoamino)-cyclohexyloxy)pyrrolo[1,2-f][1,2,4]triazin-4-amine

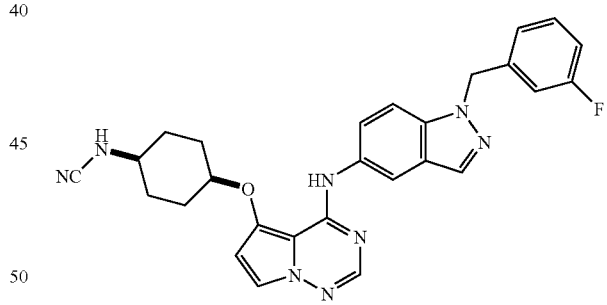

A mixture of 5 (54 mg, 0.15 mmole), cyanogen bromide (13 mg, 0.12 mmole) and sodium acetate (26 mg, 0.232 mmole) in MeOH was stirred at RT for 4 hr. Removal of the solvent followed by silica gel chromatography with EtOAc as eluent afforded the product (47 mg, 83.2%): MS: 497 (M+H)+; HPLC Ret Time: 1.92 min (Phenomenex Primesphere 5μ C4, 4.6×30 mm column, 2 min gradient, 4 mL/min).

Treatment of a sample with one equivalent of a 0.8N solution of HCl in dioxane followed by removal of the solvent afforded the hydrochloride salt: 1H NMR (DMSO-D6+D2O): 1.81–1.50 (m,6H), 2.06–1.90 (m, 2H), 3.19 (m, 1H), 4.52 (m, 1H), 5.66 (s, 3H), 6.51 (d, 1H), 7.13–6.92 (m, 3H), 7.39–7.29 (m, 1H), 7.53 (dd, 1H), 7.59 (d, 1H), 7.71 (d, 1H), 7.76 (s, 1H), 8.15 (s, 1H), 8.23 (s, 1H).

EXAMPLE 13

Methyl 4-(((1,4-trans)-4-(4-(1-(3-fluorobenzyl)-1H-indazol-5-ylamino)pyrrolo[1,2-f][1,2,4]triazin-5-yloxy)cyclohexylamino)methyl)benzoate

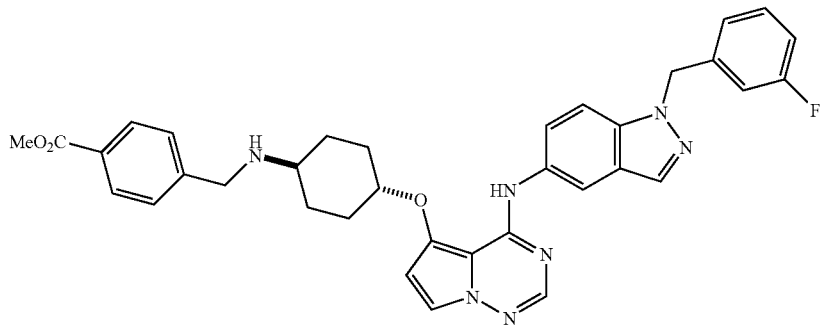

EXAMPLE 14

Methyl 4-(((1,4-cis)-4-(4-(1-(3-fluorobenzyl)-1H-indazol-5-ylamino)pyrrolo[1,2-f][1,2,4]triazin-5-yloxy)cyclohexylamino)methyl)benzoate

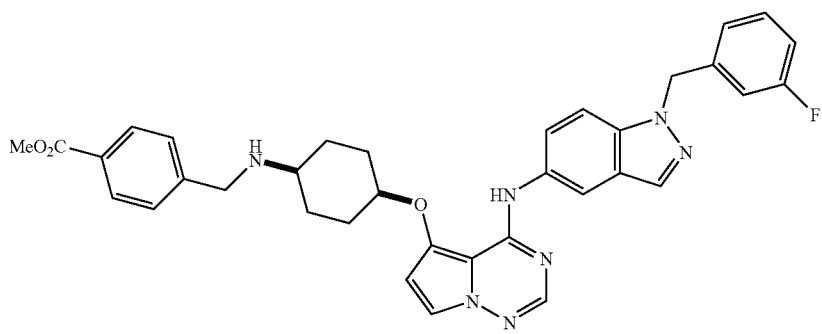

Method A. A solution of 4 (780 mg, 1.66 mmole), methyl 4-(aminomethyl)benzoate hydrochloride (402 mg, 1.99 mmole) and trimethyl orthoformate (3 ml) in DMF (15 mL) was stirred at RT for 15 min and then NaBH(OAc)$_3$ (880 mg, 4.15 mmole) was added in small portions. After 18 hr, the excess hydride was destroyed by the addition of a mixture of AcOH and MeOH (1:1; 1 mL). The resulting mixture was passed through a short pad of SCX silica gel (Silicycle brand, 10 gm), eluting first with MeOH and then a 2.0 M of NH$_3$ in MeOH to obtain a mixture of 13 and 14. These were separated by preparative HPLC (YMC ODS-A S-5 μm, 30×100 mm; CH$_3$CN:H$_2$O: 5.0 M NH$_4$OAc=1:9:0.01 to 9:1:0.01; flow=20 mL/min; gradient time=7 min). This gave 13 (260 mg, 25%): MS: 620 (M+H)$^+$; HPLC Ret Time: 1.49 min (Phenomenex Primesphere 5μ C18, 4.6×30 mm column, CH$_3$CN:H$_2$O:TFA=1:9:0.005 to 9:1:0.005, 2 min gradient, 4 mL/min); $^1$H NMR (DMSO, d-6): 1.24 (m, 2H), 1.56 (m, 2H), 1.96 (m, 2H), 2.13 (m, 2H), 3.34 (s, 3H), 3.81 (s, 2H), 4.31 (m, 1H), 5.70 (s, 2H), 6.53 (d, J=3.07 Hz, 1H), 7.02 (d, J=7.7 Hz, 2H), 7.10 (m, 1H), 7.36 (m, 1H), 7.49 (m, 3H), 7.56 (d, J=3.08 Hz, 1H), 7.71 (d, J=9.20 Hz, 1H), 7.81 (s, 1H), 7.90 (d, J=7.95 Hz, 2H), 8.15 (s, 1H), 8.31 (m, 1H), 8.33 (s, 1H) and 13 (187 mg 18%): MS: 620 (M+H)$^+$; HPLC Ret Time: 1.47 min (Phenomenex Primesphere 5μ C 18, 4.6×30 mm, CH$_3$CN:H$_2$O:TFA=1:9:0.005 to 9:1:0.005, 2 min gradient, 4 mL/min); 1H NMR (CDCl$_3$): 1.57–1.44 (m, 2H), 2.03–1.83 (m, 4H), 2.23–2.13 (m, 2H), 2.87–2.74 (m, 1H), 3.85 (s, 3H), 3.90 (s, 2H), 4.35 (broad s, 1H), 5.48 (s, 2H), 6.08 (d, J=3.03 Hz, 1H), 6.8 (dt, J=2.02, 9.09 Hz, 1H), 6.95–6.88 (m, 2H), 7.24–7.19 (m, 1H), 7.29–7.24 (m,1H), 7.31 (d, J=3.03 Hz), 7.51 (d, J=8.08 Hz, 2H), 7.68 (dd, J=2.02, 9.10 Hz, 1H), 7.80 (s, 1H), 7.91 (d, J=8.59 Hz, 2H), 7.98 (s, 1H), 8.02 (s, 1H), 8.35 (d, J=1.52 Hz, 1H).

Method B. NaBH(OAc)$_3$ (1.25 g, 7.61 mmole) was added portion wise to a stirred solution of 6 (2.39 g, 5.07 mmole) and methyl 4-formylbenzoate (1.25 g, 7.61 mmole) in dry DMF (15 mL) at RT over 3 hr. After 18 hr, more methyl 4-formylbenzoate (0.333 g, 2.03 mmole) was added and the reaction was left stirring for an additional 4 hr. The reaction was neutralized with solid NaHCO$_3$, diluted with EtOAc (400 mL) and washed with water (3×40 mL). The organic phase was dried (MgSO$_4$) and concentrated in vacuo leaving an orange thick syrup which was chromatographed on silica gel eluting with EtOAc followed by a 4% mixture of a 2 N solution of NH$_3$ in MeOH and EtOAc to give 13 (1.85 g, 59%).

EXAMPLE 15

4-(((1,4-trans)-4-(4-(1-(3-Fluorobenzyl)-1H-indazol-5-ylamino)pyrrolo[1,2-f][1,2,4]triazin-5-yloxy)cyclohexylamino)methyl)benzoic acid

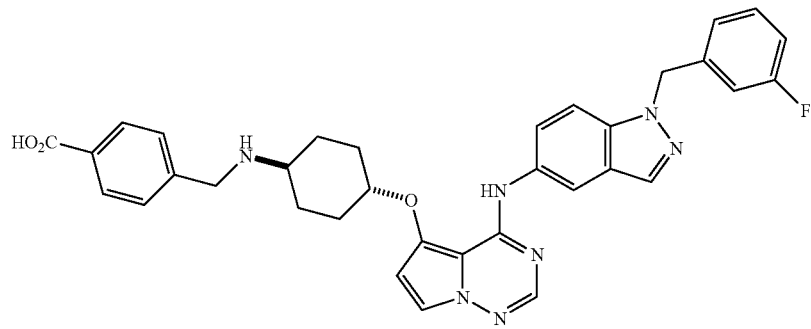

An aqueous solution of NaOH (6,86 mL, 4 N, 27.4 mmole) was added to a solution of 13 (0.425 g, 0.686 mmole) in a mixture of THF:MeOH:water (2:2:1, 30 mL). Some water was added after 1 hr to make the solution homogeneous and, after an additional hour, the mixture was neutralized with AcOH and the solvents were removed. The residue was triturated into water and the crude product was collected as a white solid. Purification by preparative HPLC (YMC ODS-A S-5-μm, 20×100 mm; eluent: $CH_3CN:H_2O$:5 M $NH_4OAc$=1:9:0.01 to 9:1:0.01; flow=20 mL/min; grad. time=7 min), afforded the product (0.353 mg, 85%): MS: 606 (M+H)+; HPLC Ret Time: 1.42 min (Phenomenex Primesphere 5, C4, 4.6×30 mm column, 2 min gradient, 4 mL/min); 1H NMR (DMSO, d-6): 1.26 (m, 2H), 1.57 (m, 2H), 1.97 (m, 2H), 2.15 (m, 2H), 3.81 (s, 2H), 4.31 (m, 1H), 5.70 (s, 2H), 6.53 (d, J=2.94 Hz, 1H), 7.02 (d, J=7.09 Hz, 2H), 7.10 (m, 1H), 7.36 (m, 1H), 7.46 (d, J=8.12 Hz, 2H), 7.51 (d, J=1.93 Hz, 1H), 7.53 (d, J=1.9 Hz, 1H), 7.56 (d, J=3.07 Hz, 1H), 7.72 (d, J=8.15 Hz, 1H), 7.81 (s, 1H), 7.90 (d, J=8.03Hz, 3H), 8.15 (s, 1H), 8.31 (m, 1H), 8.33 (s, 1H).

EXAMPLE 16

4-(((1,4-cis)-4-(4-(1-(3-Fluorobenzyl)-1H-indazol-5-ylamino)pyrrolo[1,2-f][1,2,4]triazin-5-yloxy)cyclohexylamino)methyl)benzoic acid

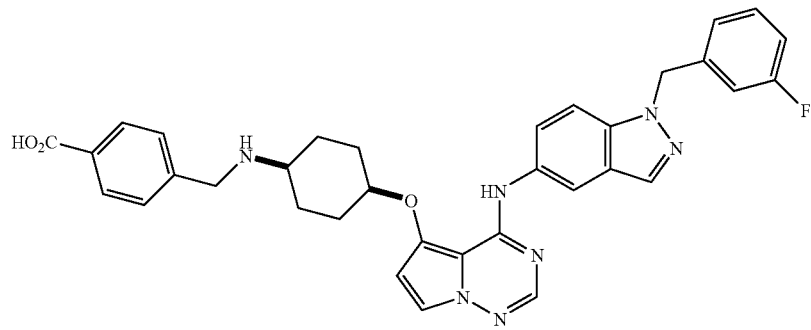

Compound 16 was prepared from 14 in the same manner as Example 15 and exhibited: MS: 606 (M+H)+; HPLC Ret Time: 1.42 min (Phenomenex Primesphere 5v C4, 4.6×30 mm column, 2 min gradient, 4 mL/min).

EXAMPLE 17

Isomer A and Isomer B 4-((4-(4-(3-chloro-4-fluorophenylamino)pyrrolo[1,2-f][1,2,4]triazin-5-yloxy)cyclohexylamino)methyl)benzoic

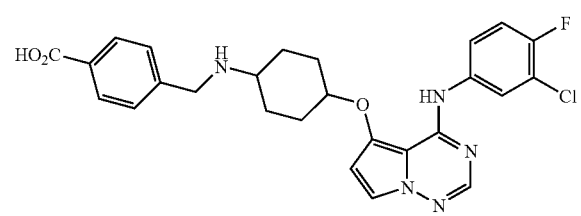

17A. Preparation of 4-(4-(3-chloro-4-fluorophenylamino)pyrrolo[1,2-f][1,2,4]triazin-5-yloxy)cyclohexanone

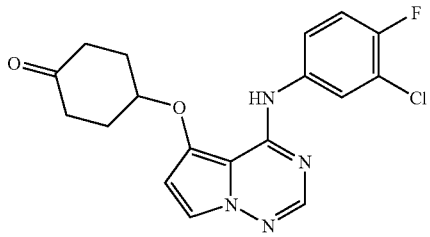

Compound 17A was prepared from 7A and 1-hydroxy-4-cyclohexanone ethylene ketal in the same manner as Example 4 and exhibited: MS: 375 (M+H)+; HPLC Ret Time: - - - min (Phenomenex Primesphere 5μ C4, 4.6×30 mm column, 2 min gradient, 4 mL/min).

17B. Preparation of 4-((4-(4-(3-Chloro-4-fluorophenylamino)pyrrolo[1,2-f][1,2,4]triazin-5-yloxy)cyclohexylamino)methyl)benzoic, isomer A and B Compound 17, isomers A and B, were prepared from 17A and methyl 4-(aminomethyl)benzoate hydrochloride in the same manner as Method A for Examples 13 and 14 followed by saponification as for Example 15. Isomer A exhibited: MS: 510 (M+H)+; HPLC Ret Time: 1.48 min (Phenomenex Primesphere 5μ C4, 4.6×30 mm column, 2 min gradient, 4 mL/min) and isomer B exhibited: MS: 510 (M+H)+; HPLC Ret Time: 1.43 min (Phenomenex Primesphere 5μ C4, 4.6×30 mm column, 2 min gradient, 4 mL/min).

EXAMPLE 18

4-(((1,4-trans)-4-(4-(3-chloro-4-(pyridin-2-ylmethoxy)phenylamino)pyrrolo-[1,2-f][1,2,4]triazin-5-yloxy)cyclohexylamino)methyl)benzoic acid

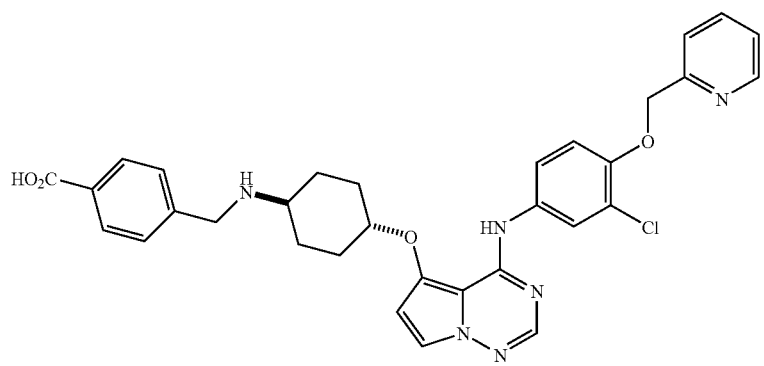

EXAMPLE 19

4-(((1,4-cis)-4-(4-(3-chloro-4-(pyridin-2-ylmethoxy)phenylamino)pyrrolo-[1,2-f][1,2,4]triazin-5-yloxy)cyclohexylamino)methyl)benzoic acid

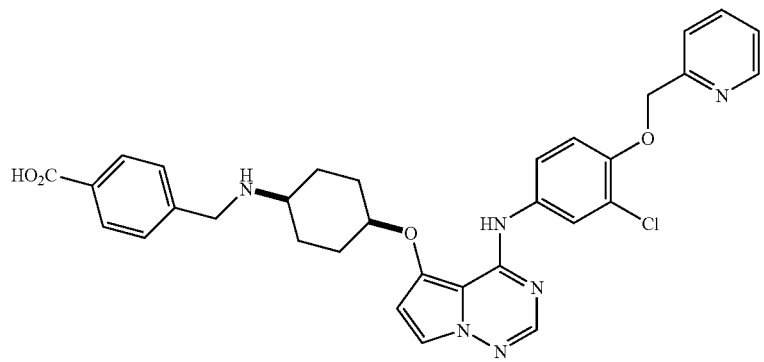

Compound 19 was prepared from 8A and 1-hydroxy-4-cyclohexanone ethylene ketal in the same manner as Example 17. Example 18 exhibited: MS: 600 (M+H)+; HPLC Ret Time: 1.44 min (Phenomenex Primesphere 5g C4, 4.6×30 mm column, 2 min gradient, 4 mL/min) and Example 19 exhibited: MS: 600 (M+H)+; HPLC Ret Time: 1.42 min (Phenomenex Primesphere 5μ C4, 4.6×30 mm column, 2 min gradient, 4 mL/min. Example 18 was also prepared from 9 and methyl 4-formylbenzoate using the method described for Example 14, Method B, followed by saponification as for Example 15.

EXAMPLE 20

Isomer A and Isomer B 2-(4-(4-(1-(3-fluorobenzyl)-1H-indazol-5-ylamino)pyrrolo[1,2-f][1,2,4]triazin-5-yloxy)cyclohexy-lamino)acetic acid

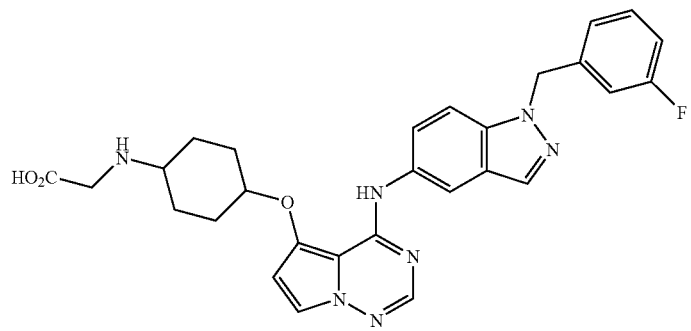

Compound 20, isomers A and B, were obtained from the ketone 4 and glycine ethyl ester hydrochloride as described for Examples 11 and 13, Method A and then saponified as described for Example 15. Isomer A exhibited: MS: 530 (M+H)+; HPLC Ret Time: 1.43 min (Phenomenex Primesphere 5μ C4, 4.6×30 mm column, 2 min gradient, 4 mL/min) and Isomer B exhibited: MS: 530 (M+H)+; HPLC Ret Time: 1.41 min (Phenomenex Primesphere 5μ C4, 4.6×30 mm column, 2 min gradient, 4 mL/min).

EXAMPLE 21

Isomer A and Isomer B 1-(4-(4-(1-(3-fluorobenzyl)-1H-indazol-5-ylamino)pyrrolo[1,2-f][1,2,4]triazin-5-yloxy)cyclohexy-lamino)cyclopropanecarboxylic acid

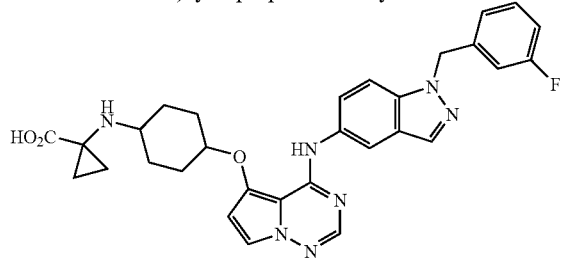

Compound 21, isomers A and B, were obtained from the ketone 4 and 1-aminocyclopropanecarboxylic acid ethyl ester hydrochloride as described for Example 20. Isomer A exhibited: MS: 556 (M+H)+; HPLC Ret Time: 1.40 min (Phenomenex Primesphere 5μ C4, 4.6×30 mm column, 2 min gradient, 4 mL/min) and Isomer B exhibited: MS: 556 (M+H)+; HPLC Ret Time: 1.40 min (Phenomenex Primesphere 5μ C4, 4.6×30 mm column, 2 min gradient, 4 mL/min).

EXAMPLE 22

3-((1,4-trans)-4-(4-(1-(3-fluorobenzyl)-1H-indazol-5-ylamino)pyrrolo[1,2-f][1,2,4]triazin-5-yloxy)cyclohexylamino)-2,2-dimethylpropanoic acid

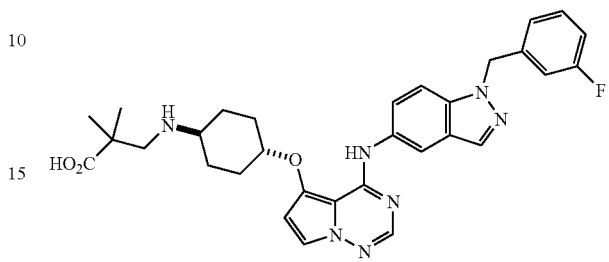

NaBH(OAc)3 (32 mg, 0.15 mmole) was added to a stirred suspension of 5 (50 mg, 0.11 mmole), ethyl 2,2-dimethyl-3-oxopropanoate (15 mg, 0.11 mmole) and HOAc (9 μL, 0.13 mmole) in dry 1,2-dichloroethane (1 mL) at RT. After 20 min, the reaction was quenched with aqueous NaOH (2 mL, 1.0 N) and extracted with EtOAc. The organic phase was washed with brine, dried (Na2SO4), and the solvents removed. The residue was chromatographed (radial chromatography with a step gradient of DCM containing 0, 1, 2, 3, 4% MeOH) to give ethyl 3-((1,4-trans)-4-(4-(1-(3-fluo-robenzyl)-1H-indazol-5-ylamino)pyrrolo[1,2-f][1,2,4]tri-azin-5-yloxy)cyclohexylamino)-2,2-dimethylpropanoate (60 mg, quantitative yield): MS: 600 (M+H)+; HPLC Ret Time: 2.05 min (YMC Xterra S5 4.6×50 mm column, 3 min gradient, 4 mL/min). A mixture of this ester (63 mg, 0.11 mmole) and an aqueous solution of LiOH (0.55 mL, 1.0 M, 0.55 mmole) in MeOH (5 mL) under N2 was heated at 40° C. for 39 hr. The reaction was poured onto a SCX cartridge (Varian Mega Bond Elut SCX, 1 gm) that had been conditioned with MeOH. This was washing with 1 column volume of MeOH followed by several column volumes of a 2.0 N solution of NH3 in MeOH. Removal of the solvent from the appropriate fractions left the product as a glass (48 mg, 76%): MS: 572 (M+H)+; HPLC Ret Time: 1.88 min (YMC Xterra S5 4.6×50 mm column, 3 min gradient, 4 mL/min).

EXAMPLE 23

3-((1,4-cis)-4-(4-(1-(3-fluorobenzyl)-1H-indazol-5-ylamino)pyrrolo[1,2-f][1,2,4]triazin-5-yloxy)cyclohexylamino)-2,2-dimethylpropanoic acid

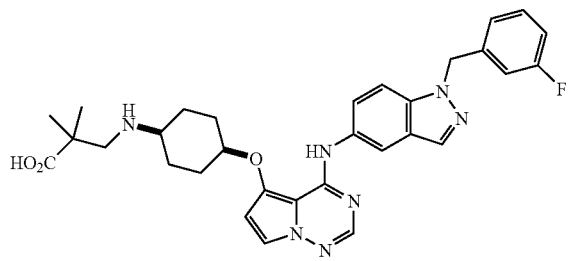

Compound 23 was obtained from the amine 4 and ethyl 2,2-dimethyl-3-oxopropanoate as described for Examples 22 and exhibited: MS: 572 (M+H)$^+$; HPLC Ret Time: 1.33 min (YMC Xterra S5 4.6×50 mm column, 2 min gradient, 4 mL/min).

EXAMPLE 24

Isomer A and Isomer B

N-(4-((4-(4-(1-(3-fluorobenzyl)-1H-indazol-5-ylamino)pyrrolo[1,2-f][1,2,4]triazin-5-yloxy)cyclohexylamino)methyl)phenylsulfonyl)acetamide mmole) in a mixture of DCM (50 mL) and EtOH (7 mL). After the reaction was complete, it was diluted with DCM, washed with water, and dried (Na$_2$SO$_4$). The solvent was removed to leave the crude carbamic acid, [[4-(aminosulfonyl)phenyl]methyl]-tert-butyl ester. A portion of this (1.29 gm, 4.49 mmole) was added to a stirred suspension of K$_2$CO$_3$ (1.24 gm, 8.99 mmole) in acetone (18 mL) followed by acetyl chloride (0.42 mL, 5.84 mmole) and the mixture was heated at reflux for 16 hr. Further acetyl chloride (0.42 mL, 5.84 mole) was added and heating was continued for and additional 1.5 hr. After cooling to RT, water was added to give a clear solution which was extracted with EtOAc. The organic phase was washed with brine, dried (Na$_2$SO$_4$), and the solvent removed. Silica gel column chromatography (elution with a mixture of DCM and MeOH) afforded the carbamic acid, [[4-(N-acetyl-aminosulfonyl)phenyl]methyl]-tert-butyl ester (1.14 gm, 77%) as a solid: $^1$H NMR (CDCl$_3$): 1.46 (s, 9H), 2.05 (s, 3H), 4.39 (br s, 2H), 5.0 (br s, 1H), 7.44 (d, 2H), 7.99 (d, 2H), 8.5 (br s, 1H). This (1.29 gm 3.93 mmole) was dissolved in a mixture of dry DCM (40 mL) and TFA (30 mL) in an ice bath. After 1 hr, the solvent was removed to leave the TFA salt of the final product. Material was converted to the free base by application onto a SCX column (Varian Mega Bond Elut SCX) that had been conditioned with MeOH. This was washing with 1 column volume of MeOH followed by several column volumes of a 2.0 N solution of NH$_3$ in MeOH. Removal of the solvent from the appropriate fractions left the product as a glass: MS: 229 (M+H)$^+$; HPLC Ret Time: 0.12 min (YMC Xterra S7 3.0×50 mm column, 3 min gradient, 4 mL/min).

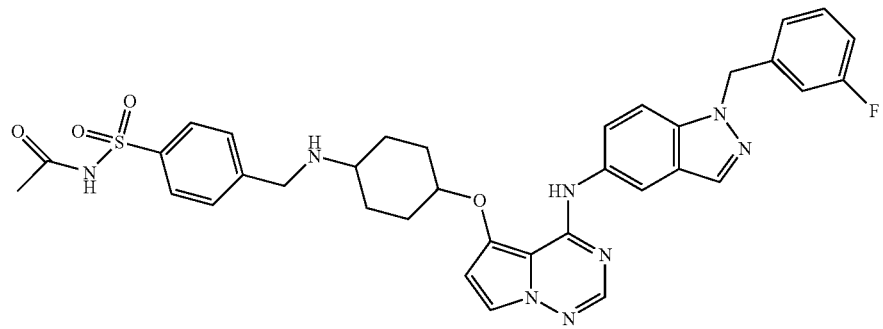

24A. Preparation of N-(4-(aminomethyl)phenylsulfonyl)acetamide

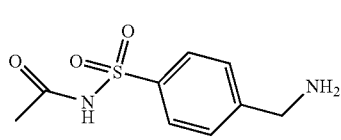

Di-tert-butyl dicarbonate (4.80 gm, 22 mmole) was added to a solution of 4-(aminomethyl)benzenesulfonamide hydrogen chloride (4.45 gm, 20 mmole) and TEA (6.14 mL, 44

24B. Preparation of N-(4-((4-(4-(1-(3-fluorobenzyl)-1H-indazol-5-ylamino)pyrrolo[1,2-f][1,2,4]triazin-5-yloxy)cyclohexylamino)methyl)-phenylsulfonyl)acetamide NaBH(OAc)$_3$ (60 mg, 0.15 mmole) was added to a stirred mixture of 3 (94 mg, 0.20 mmole), N-(4-(aminomethyl)phenylsulfonyl)acetamide (46 mg, 0.20 mmole) and HOAc (16 μL, 0.26 mmole) in a mixture of dry DCM (0.4 mL) and dry DMF (0.4 mL) at RT. After 20 min, the reaction was quenched with aqueous NaOH (2 mL, 1.0 N) and then neutralized with aqueous 1.0 N HCl. This was extracted with EtOAc and extracts were washed with brine, dried (Na$_2$SO$_4$), and the solvents removed. The residue was chromatographed (radial chromatography with a step gradient of DCM containing 0, 1, 2, 3, 4, 5% of a 2.0 N methanolic solution of NH₃) to give Isomer A (19 mg, 11%): MS: 683 (M+H)⁺; HPLC Ret Time: 1.18 min (YMC Xterra S7 3.0×50 mm column, 2 min gradient, 5 mL/min) and Isomer B MS: 683 (M+H)⁺; HPLC Ret Time: 1.18 min (YMC Xterra S7 3.0×50 mm column, 2 min gradient, 5 mL/min).

EXAMPLE 25

4-(((1,4-trans)-4-(4-(1-(3-Fluorobenzyl)-1H-indazol-5-ylamino)pyrrolo[1,2-f][1,2,4]triazin-5-yloxy)cyclohexylamino)methyl)-N-(methylsulfonyl)benzamide

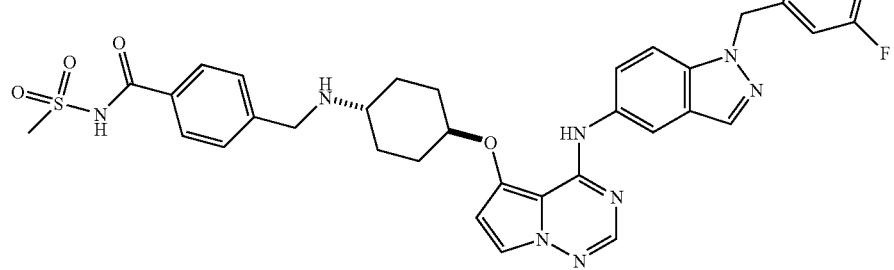

A suspension of 15 (240 mg, 0.396 mmole) in dry DMF (8 mL) was treated with di-tert-butyl dicarbonate (104 mg, 0.477 mmole) and stirred at 50° C. for 16 hr. This was concentrated in vacuo to dryness to leave the crude 4-((N-tert-butyloxycarbonyl-(1,4-trans)-4-(4-(1-(3-fluorobenzyl)-1H-indazol-5-ylamino)pyrrolo[1,2-f][1,2,4]triazin-5-yloxy)cyclohexylamino)methyl)-N-(methylsulfonyl)benzamide which was used without further purification: HPLC Ret Time 1.92 min (Phenomenex Primesphere 4.6×30 mm 5µ C18-HC column; CH₃CN:H₂O:TFA=1:9:0.005 to 9:1:0.005, 2 min gradient, 4 mL/min). A mixture of this crude acid (36.7 mg, 0.052 mmole), CH₃SO₂NH₂ (6.4 mg, 0.0674 mmole), DMAP (10.76 mg, 0.088 mmole) and 1-(3-dimethylaminopropyl)-3-ethylcarbodiimide hydrochloride (16.9 mg, 0.088 mmol) in dry DCM (1 mL) was stirred at RT for 3 hr. The mixture was diluted with CHCl₃ and washed with water. The organic phase was dried (MgSO₄) and concentrated in vacuo. Flash chromatography on silica gel (elution with EtOAc:DCM (9:1) followed by a step gradient varied from 0 to 10% MeOH in AcOEt) afforded 4-((N-tert-butyloxycarbonyl-(1,4-trans)-4-(4-(1-(3-fluorobenzyl)-1H-indazol-5-ylamino)pyrrolo[1,2-f][1,2,4] triazin-5-yloxy)cyclohexylamino)methyl)-N-(methylsulfonyl)benzamide (23 mg, 56%): MS: 783(M+H)⁺; ¹H NMR (DMSO, d-6): 1.0–1.8 (m, 15H), 2.21 (m, 2H), 2.88 (s, 3H), 4.20 (m, 1H), 4.36 (m, 2H), 5.73 (s, 2H), 6.49 (d, J=3.08 Hz, 1H), 7.02 (d, J=7.02 Hz, 2H), 7.15 (m, 1H), 7.19 (d, J=8.17 Hz, 3H), 7.36 (m, 1H), 7.53 (m, 3H), 7.73 (d, J=8.61 Hz, 1H), 7.79 (s, 1H), 7.87 (d, J=8.08 Hz, 3H), 8.15 (s, 1H), 8.30 (s, 1H), 8.34 (s, 1H). This material (23 mg, 0.029 mmole) was dissolved in dry DCM (12 mL) and treated with TFA (1 mL) at RT. After 2 hr, this was diluted with toluene and concentrated to dryness. Preparative HPLC (YMC ODS-A S-5 µm, 20×100 mm column; gradient of CH₃CN:H₂O: 5.0 M NH₄OAc=20% (1:9:0.01) to 100% (9:1:0.01); flow=20 mL/min; 7 min gradient with an initial hold of 4 min) afforded the product (14 mg, 71%): MS: 683 (M+H)⁺; LCMS Ret Time: 1.48 min (Phenomenex Primesphere 5µ C18-HC 4.6×30 mm column; 2 min gradient, 4 mL/min); ¹H NMR (DMSO, d-6): 1.5 (m, 2H), 1.63 (m, 2H), 2.20 (m, 2H), 2.25 (m, 2H), 2.84 (s, 3H), 4.21 (m, 1H), 4.28 (m, 2H), 5.69 (s, 2H), 6.58 (d, J=2.44 Hz, 1H), 7.00 (m, 2H), 7.09 (dt, J=2.7 and 8.9 Hz, 2H),), 7.35 (m, 1H), 7.43 (d, J=7.3Hz, 2H), 7.53 (dd, J=9.3 and 3.0 Hz, 1H), 7.57 (d, J=3.04 Hz, 1H), 7.71 (d, J=9.05 Hz, 1H), 7.80 (s, 1H), 7.98 (d, J=7.36 Hz, 2H), 8.14 (s, 1H), 8.28 (s, 1H), 8.32 (s, 1H), 8.75 (m, 1H).

EXAMPLE 26

4-(1-(3-fluorobenzyl)-1H-indazol-5-ylamino)pyrrolo[1,2-f][1,2,4]triazin-5-yl methyl carbonate

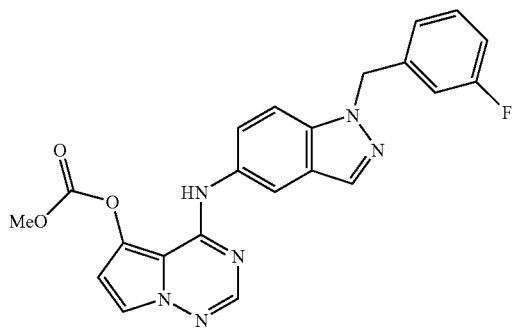

Methyl chloroformate (10 mg, 0.1 mmole) was added to a stirred solution of 1 (25 mg, 0.067 mmole) and triethylamine (5 drops) in THF at RT. After 10 min, the solvent was removed and the reaction product chromatographed on silica gel (EtOAc:hexane=1:1). The product was dissolved in THF and treated with one equivalent of 0.8N solution of HCl in dioxane. Removal of the solvent followed by trituration with ether gave the HCl salt (18 mg, 57%): MS: 433 (M+H)⁺; LCMS Ret Time: 1.81 min (Phenomenex Primesphere 5µ C18-HC 4.6×30 mm column, 2 min gradient, 4 mL/min); ¹H NMR (DMSO-D₆): 3.88 (s, 3H), 5.71 (s, 2H), 6.71 (d, 1H), 7.07–6.98 (m, 2H), 7.11 (dt, 1H), 7.41–7.32 (m, 1H), 7.55 (d, 1H), 7.71 (d, 1H), 7.74 (d, 1H), 7.90 (s, 1H), 8.11 (s, 1H), 8.17 (s, 1H), 8.99 (s, 1H).

EXAMPLE 27

4-(1-(3-Fluorobenzyl)-1H-indazol-5-ylamino)pyrrolo[1,2-f][1,2,4]triazin-5-yl methylcarbamate

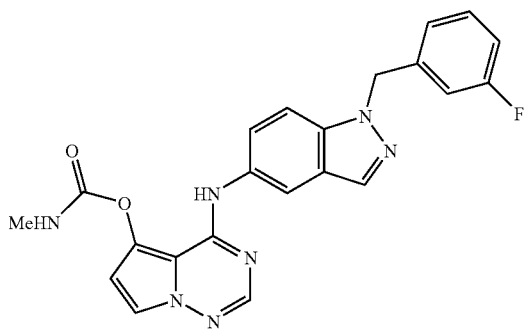

A solution of 1 (25 mg, 0.067 mmole), methyl isocyanate (4 mg, 0.07 mmole) and DMAP (8 mg, 0.07 mmole) in DCM was stirred at RT for 6 hr. Removal of the solvent followed by chromatography on silica gel (elution with 25 to 50% EtOAc in hexane) afforded the product (20 mg, 69%). It was treated with one equivalent of an 0.8N solution of HCl in dioxane to give the HCl salt: MS: 432 (M+H)$^+$; LCMS Ret Time: 1.66 min (Phenomenex Primesphere 5 μ C18-HC 4.6×30 mm column, 2 min gradient, 4 mL/min); $^1$H NMR (DMSO-D$_6$+D$_2$O): 2.71 (s, 3H), 5.69 (s, 2H), 6.80 (d, 1H), 7.13–6.96 (m, 3H), 7.39–7.31 (m, 1H), 7.52 (dd, 1H), 7.69 (d, 1H), 7.77 (d, 1H), 7.80 (s, 1H), 8.04 (d, 1H), 8.2 (s, 1H).

EXAMPLE 28

N-(1-(3-Fluorobenzyl)-1H-indazol-5-yl)-5-(tetrahydro-2H-thiopyran-4-yloxy)pyrrolo[1,2-f][1,2,4]triazin-4-amine

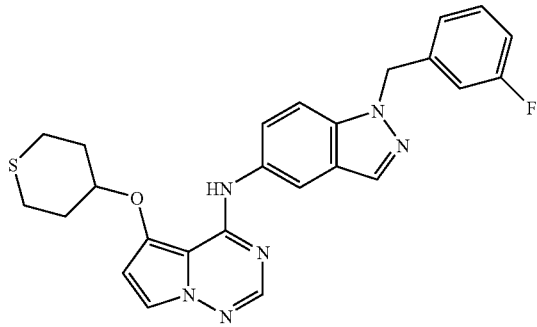

Compound 28 was obtained from the 1 and glycine tetrahydro-2H-thiopyran-4-ol as described for Example 3 and exhibited: MS: 475 (M+H)$^+$; HPLC Ret Time: 1.54 min (YMC Xterra S7 3.0×50 mm column, 2 min gradient, 5 mL/min).

EXAMPLE 29

N-(1-(3-Fluorobenzyl)-1H-indazol-5-yl)-5-(1-oxotetrahydro-2H-thiopyran-4-yloxy)pyrrolo[1,2-f][1,2,4]triazin-4-amine

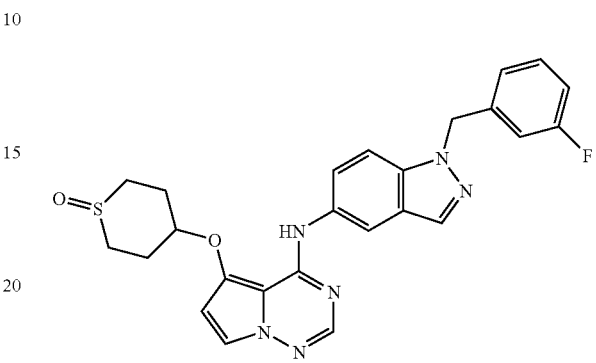

EXAMPLE 30

N-(1-(3-Fluorobenzyl)-1H-indazol-5-yl)-5-(1,1-dioxotetrahydro-2H-thiopyran-4-yloxy)pyrrolo[1,2-f][1,2,4]triazin-4-amine Solid m-chloroperbenzoic acid (68 mg, 77%, 0.3 mmole) was added to a solution of 28 (143 mg, 0.3 mmole) in CHCl$_3$ (3 mL) at −30° C. After 50 min, an aq. solution of NaHSO$_3$ (6%, 0.5 mL) was added and the reaction was allowed to warm to RT. This was diluted with CHCl$_3$ and extracted with a saturated aq. solution of NaHCO$_3$ (2×) and dried (Na$_2$SO$_4$). Removal of the solvent followed by radial chromatography (step gradient elution with DCM containing 0 to 3% MeOH gave the 29 (138 mg, 93%): MS: 491 (M+H)$^+$; LCMS Ret Time: 1.66 min (Phenomenex Primesphere 5μ C4; 4.6×30 mm column, 2 min gradient, 4 mL/min and 30 (6 mg, 4%): MS: 507 (M+H)$^+$; LCMS Ret Time: 2.53 min (Phenomenex Primesphere 5μ C4; 4.6×30 mm column, 4 min gradient, 4 mL/min.

EXAMPLE 31

Isomer A and B

N-(1-(3-Fluorobenzyl)-1H-indazol-5-yl)-5-(1-imino-1-oxotetrahydro-2H-thiopyran-4-yloxy)pyrrolo[1,2-f][1,2,4]triazin-4-amine

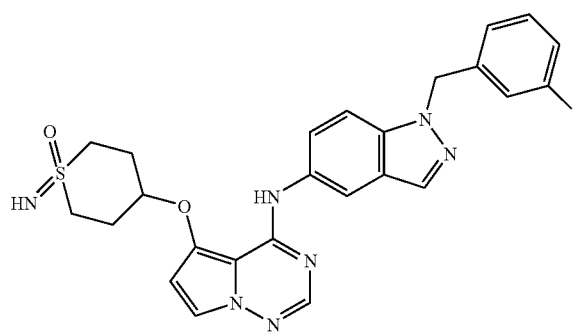

A mixture of 29 (95 mg, 0.19 mmole) and NaN$_3$ (100 mg, 0.80 mmole) in polyphosphoric acid (5 gm) was heated at 56° C. for 12 hr and then 60° C. for 2 hr. After cooling to RT, water was added and the pH was adjusted to 11 using 50% aq. NaOH. The reaction was extracted with DCM and the organic extracts were dried (Na$_2$SO$_4$). Removal of the solvents followed by radial chromatography (step gradient elution with DCM containing 0 to 3% MeOH) afforded Isomer A (13 mg, 13%): MS: 506 (M+H)$^+$; HPLC Ret Time: 1.03 min (YMC Xterra S7 3.0×50 mm column, 2 min gradient, 5 mL/min) and Isomer B (30 mg, 30%): MS: 506 (M+H)$^+$; HPLC Ret Time: 1.05 min (YMC Xterra S7 3.0×50 mm column, 2 min gradient, 5 mL/min).

EXAMPLE 32

N-(1-(3-Fluorobenzyl)-1H-indazol-5-yl)-5-(1-methylimino-1-oxotetrahydro-2H-thiopyran-4-yloxy)pyrrolo[1,2-f][1,2,4]triazin-4-amine

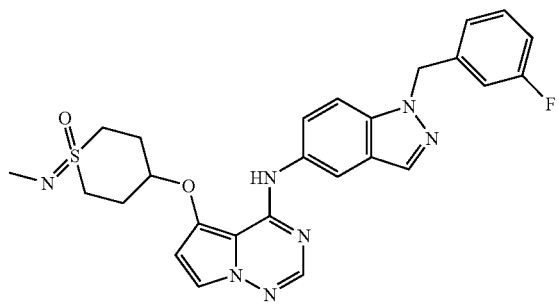

TFA (15 μL, 0.13 mmole) was added to a stirred mixture of Example 31 isomer B (21 mg, 0.042 mmole), paraformaldehyde (10 mg), triethylsilane (20 μL, 0.125 mmole) in acetonitrile (0.5 mL) at RT under N2. After 18 hr, this was diluted with water and the pH adjusted to 11 with a saturated aq. solution of Na2CO3. This was extracted with a 10% solution of MeOH in DCM (4×) and the extracts were dried (Na2SO4). Removal of the solvents followed by radial chromatography (step gradient elution with DCM containing 0 to 3% MeOH) afforded the product (12 mg, 57%): MS: 520 (M+H)+; HPLC Ret Time: 1.01 min (YMC Xterra S7 3.0×50 mm column, 2 min gradient, 5 mL/min).

EXAMPLE 33

N-((1,4-cis)-4-(4-(1-(3-fluorobenzyl)-1H-indazol-5-ylamino)pyrrolo[1,2-f][1,2,4]triazin-5-yloxy)cyclohexyl)-2-aminoacetamide

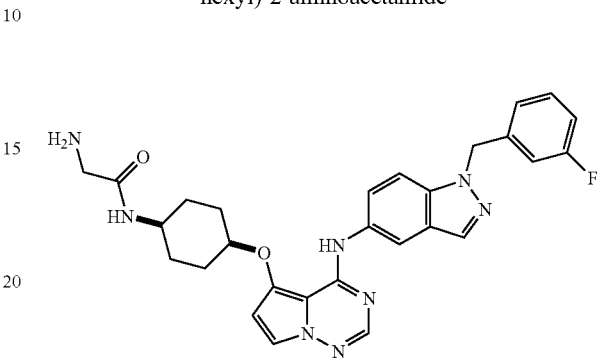

DIPEA (0.087 mL, 0.381 mmole) was added to a stirred suspension of 5 (60 mg, 0.127 mmole), Fmoc-Gly-OH (38 mg, 0.127 mmole) and benzotriazol-1-yloxytripyrrolidinophosphonium hexafluorophosphate (73 mg, 140 mmole) in dry DCM (2 mL) at RT. After 0.5 hr, this was diluted with EtOAc, washed with water, saturated NaHCO$_3$, and dried (Na$_2$SO$_4$). Radial chromatography (step gradient elution with 75 to 85% EtOAc in hexane) afforded (9H-fluoren-9-yl)methyl 2-((1,4-cis)-4-(4-(1-(3-fluorobenzyl)-1H-indazol-5-ylamino)pyrrolo[1,2-f][1,2,4]triazin-5-yloxy)cyclohexylamino)-2-oxoethylcarbamate (93 mg, 0.12 mmole). This was suspended in dry acetonitrile (2 mL) at RT and treated with piperidine (0.4 mL). After 0.5 hr, this was concentrated in vacuo. Radial chromatography (step gradient elution with 0 to 6% of a 2.0 N methanolic solution of NH$_3$ in DCM) afforded the product (60 mg, 95%): MS: 529 (M+H)$^+$; HPLC Ret Time: 1.95 min (YMC Xterra S5 4.6×50 mm column, 3 min gradient, 4 mL/min).

EXAMPLE 34

N-((1,4-trans)-4-(4-(1-(3-fluorobenzyl)-1H-indazol-5-ylamino)pyrrolo[1,2-f][1,2,4]triazin-5-yloxy)cyclohexyl)-2-aminoacetamide

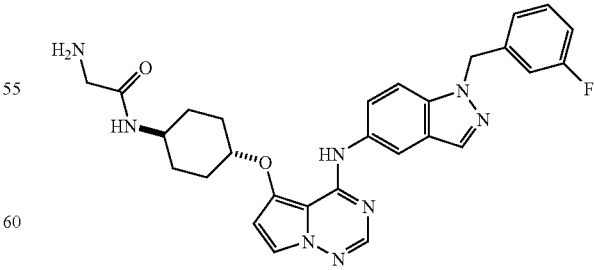

Compound 34 was obtained from 6 as described for Example 33 and exhibited: MS: 529 (M+H)$^+$; HPLC Ret Time: 1.85 min (YMC Xterra S5 4.6×50 mm column, 3 min gradient, 4 mL/min).

EXAMPLE 35

1-(3-(4-(1-(3-Fluorobenzyl)-1H-indazol-5-ylamino)pyrrolo[1,2-f][1,2,4]triazin-5-yloxy)azetidin-1-yl)-2-aminoethanone

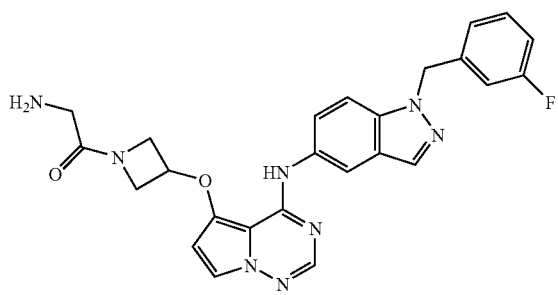

35A. Preparation of N-(1-(3-Fluorobenzyl)-1H-indazol-5-yl)-5-(1-benzhydrylazetidin-3-yloxy)pyrrolo[1,2-f][1,2,4]triazin-4-amine

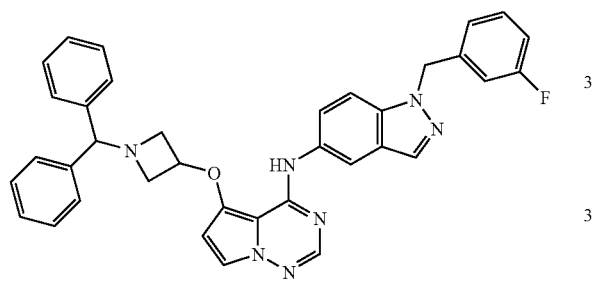

Compound 35A was obtained from 1 and 1-benzhydrylazetidin-3-ol as described for Example 5A except that the reaction was heated at 60° C. for 3 hr prior to workup. It exhibited: MS: 596 (M+H)$^+$; HPLC Ret Time: 2.17 min (YMC Xterra S5 4.6×50 mm column, 3 min gradient, 4 mL/min).

35B. Preparation of N-(1-(3-fluorobenzyl)-1H-indazol-5-yl)-5-(azetidin-3-yloxy)pyrrolo[1,2-f][1,2,4]triazin-4-amine

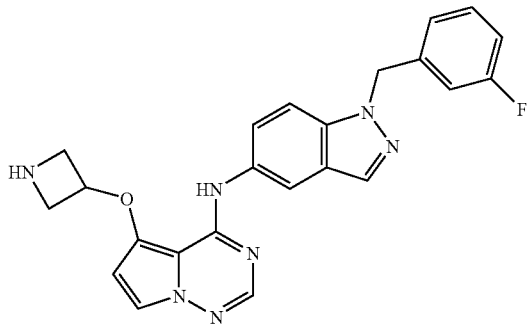

A mixture of 35A (148 mg, 0.25 mmole), palladium hydroxide (150 mg, 20 wt. % on C, wet) and 1.0 M HCl (0.25 mL) in EtOH (20 mL) was hydrogenated (55 psi, Parr apparatus) for 24 hr. After removal of the catalyst and solvent, the residue was suspended in DCM, washed with a saturated aq. solution of $Na_2CO_3$, dried ($Na_2SO_4$) and the solvent removed. Radial chromatography (step gradient elution with 0 to 15% MeOH in DCM) afforded the product (62 mg, 58%): MS: 430 (M+H)$^+$; HPLC Ret Time: 1.50 min (YMC Xterra S5 4.6×50 mm column, 3 min gradient, 4 mL/min).

35C. Preparation of 1-(3-(4-(1-(3-Fluorobenzyl)-1H-indazol-5-ylamino)pyrrolo[1,2-f][1,2,4]triazin-5-yloxy)azetidin-1-yl)-2-aminoethanone Compound 35 was obtained from 35B and Fmoc-Gly-OH as described for Example 33 and exhibited: MS: 487 (M+H)$^+$; HPLC Ret Time: 1.57 min (YMC Xterra S5 4.6×50 mm column, 3 min gradient, 4 mL/min).

EXAMPLE 36

1-(4-(4-(1-(3-Fluorobenzyl)-1H-indazol-5-ylamino)pyrrolo[1,2-f][1,2,4]triazin-5-yloxy)piperidin-1-yl)-2-aminoethanone

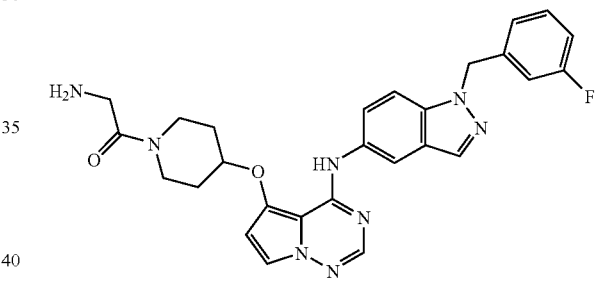

36A. Preparation of N tert-butyl 4-(4-(1-(3-fluorobenzyl)-1H-indazol-5-ylamino)pyrrolo[1,2-f][1,2,4]triazin-5-yloxy)piperidine-1-carboxylate

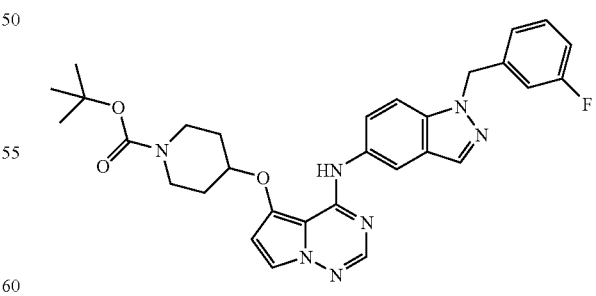

Compound 36A was obtained from 1 and tert-butyl 4-hydroxy-1-piperidinecarboxylate as described for Example 5A and exhibited: MS: 558 (M+H)$^+$; HPLC Ret Time: 2.60 min (YMC Xterra S5 4.6×50 mm column, 3 min gradient, 4 mL/min).

36B. Preparation of N-(1-(3-Fluorobenzyl)-1H-indazol-5-yl)-5-(piperidin-4-yloxy)pyrrolo[1,2-f][1,2,4]triazin-4-amine

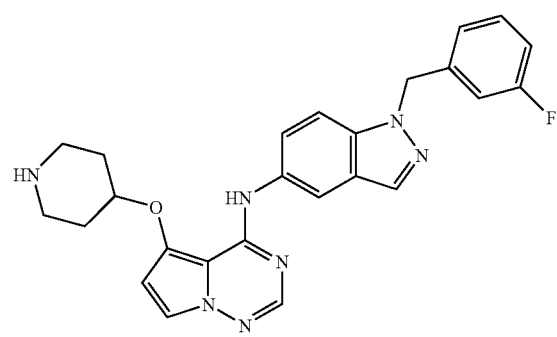

Compound 36B was obtained from 36A as described for Example 5B and exhibited: MS: 458 (M+H)+; HPLC Ret Time: 1.73 min (Phenomenex Primesphere 5μ C18-HC 4.6×30 mm column, 3 min gradient, 4 mL/min).

36C. Preparation of 1-(4-(4-(1-(3-Fluorobenzyl)-1H-indazol-5-ylamino)pyrrolo[1,2-f][1,2,4]triazin-5-yloxy)piperidin-1-yl)-2-aminoethanone Compound 36 was obtained from 36B and Fmoc-Gly-OH as described for Example 33 and exhibited: MS: 515 (M+H)+; HPLC Ret Time: 2.06 min (Phenomenex Primesphere 5μ C 18-HC 4.6×30 mm column, 3 min gradient, 4 mL/min).

EXAMPLE 37

Enantiomer A and B (1R,2R,5S)- and (1S,2S,5R)-5-(4-(1-(3-fluorobenzyl)-1H-indazol-5-ylamino)pyrrolo[1,2-f][1,2,4]triazin-5-yloxy)-2-aminocyclohexanol

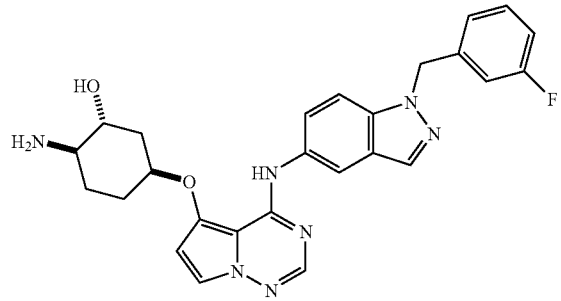

Racemic C (1S,2S,4S) and (1R,2R,4R)-4-(4-(1-(3-fluorobenzyl)-1H-indazol-5-ylamino)pyrrolo[1,2-f][1,2,4]triazin-5-yloxy)-2-aminocyclohexanol

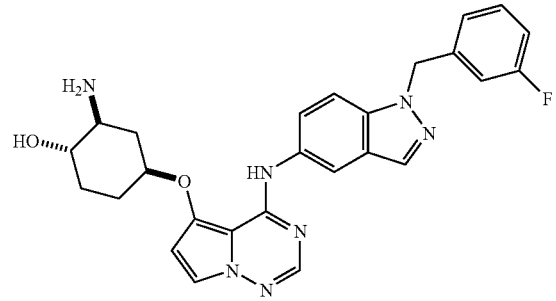

37A. Preparation of N-(1-(3-fluorobenzyl)-1H-indazol-5-yl)-5-((1S,3S,6R) and (1R,3R,6S)-7-oxa-bicyclo[4.1.0]heptan-3-yloxy)pyrrolo[1,2-f][1,2,4]triazin-4-amine

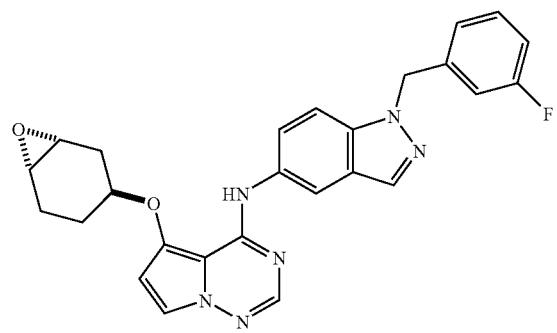

Compound 37A was obtained from 1 and cis-3,4-epoxycyclohexanol (K. B. Sharpless et al., J. Amer. Chem. Soc., 1973, 95, 6136) as described for Example 5A and exhibited: MS: 471 (M+H)+; HPLC Ret Time: 1.42 min (YMC Xterra S5 3.0×50 mm column, 2 min gradient, 5 mL/min).

37B. Preparation of Regioisomer A, (1R,2R,5S) and (1S,2S,5R)-5-(4-(1-(3-fluorobenzyl)-1H-indazol-5-ylamino)pyrrolo[1,2-f][1,2,4]triazin-5-yloxy)-2-azidocyclohexanol

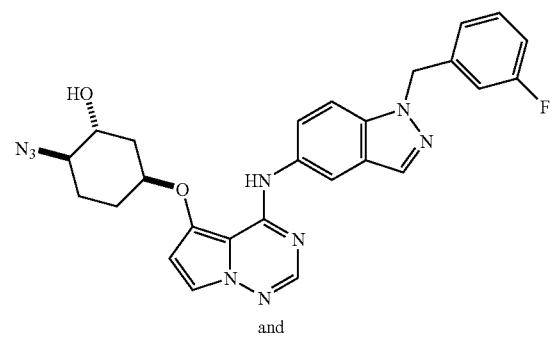

and

Regioisomer B, (1S,2S,4S) and (1R,2R,4R)-4-(4-(1-(3-fluorobenzyl)-1H-indazol-5-ylamino)pyrrolo[1,2-f][1,2,4]triazin-5-yloxy)-2-azidocyclohexanol

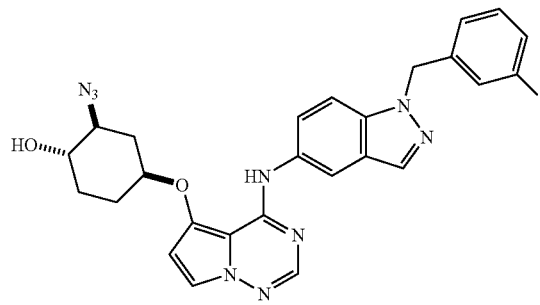

A mixture of anhydrous LiClO₄ (165 mg, 1.55 mmole) 37B (73 mg, 0.155 mmole) and NaN₃ (50 mg, 0.776 mmole) in dry CH₃CN (1.5 mL) was heated at 80° C. overnight. After cooling to RT, this was diluted with EtOAc, washed with water, dried (Na₂SO₄) and the solvents removed. Preparative HPLC (YMC S5 ODS 20×100 mm, MeOH: H₂O:TFA=1:9:0.1 to 9:1:0.1, 30 min gradient, 25 mL/min) followed by removal of solvents and liberation of the free base (partitioned between EtOAc and saturated aq. Na₂CO₃) afforded regioisomer A (25 mg, 31%): MS: 514 (M+H)⁺; HPLC Ret Time: 1.53 min (YMC Xterra S5 3.0×50 mm column, 2 min gradient, 5 mL/min) and regioisomer B (21 mg, 26%): MS: 514 (M+H)⁺; HPLC Ret Time: 1.40 min (YMC Xterra S5 3.0×50 mm column, 2 min gradient, 5 mL/min).

37C. Preparation of (1R,2R,5S)- and (1S,2S,5R)-5-(4-(1-(3-fluorobenzyl)-1H-indazol-5-ylamino)pyrrolo[1,2-f][1,2,4]triazin-5-yloxy)-2-aminocyclohexanol Enantiomer A and Enantiomer B A mixture of 37B regioisomer A (24 mg, 0.046 mmole), triphenylphosphine (24 mg, 0.92 mmole) in THF (1 mL) containing water (0.050 mL) was heated at reflux for 2 hr. This was diluted with EtOAc, dried (Na₂SO₄), and the solvent removed. Radial chromatography (silica gel, step gradient elution with mixtures of DCM containing 4 to 5% of a 2.0 N methanolic solution of NH₃) afforded the racemic product (15 mg, 77%): MS: 488 (M+H)⁺; HPLC Ret Time: 1.11 min (YMC Xterra S5 3.0×50 mm column, 2 min gradient, 5 mL/min). A sample of this racemate was separated by chiral HPLC (Chiralpak AD column, 4.6×250 mm, 10 μm, eluting with 0.05% TEA in EtOH, flow 0.7 m/min) to give Enantiomer A: Ret Time: 22.97 min and Enantiomer B: Ret Time: 29.13 min.

37D. (1S,2S,4S) and (1R,2R,4R)-4-(4-(1-(3-fluorobenzyl)-1H-indazol-5-ylamino)pyrrolo[1,2-f][1,2,4]triazin-5-yloxy)-2-aminocyclohexanol.

This was obtained from regioisomer B and triphenylphosphine as described for Example 37A and the racemic product exhibited: MS: 488 (M+H)⁺; HPLC Ret Time: 1.09 min (YMC Xterra S7 3.0×50 mm column, 3 min gradient, 5 mL/min).

EXAMPLE 38

Enantiomer A and B (1R,2R,5R) and (1S,2S,5S)-5-(4-(1-(3-fluorobenzyl)-1H-indazol-5-ylamino)pyrrolo[1,2-f][1,2,4]triazin-5-yloxy)-2-aminocyclohexanol

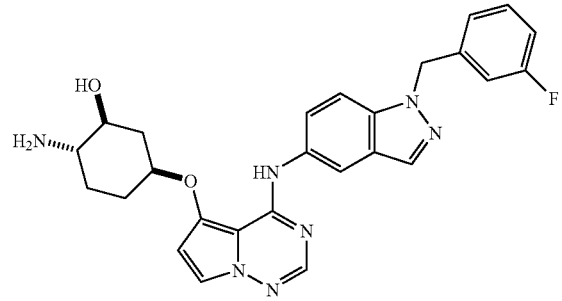

Racemic Regioisomer C (1S,2S,4R) and (1R,2R,4S)-4-(4-(1-(3-fluorobenzyl)-1H-indazol-5-ylamino)pyrrolo[1,2-f][1,2,4]triazin-5-yloxy)-2-aminocyclohexanol

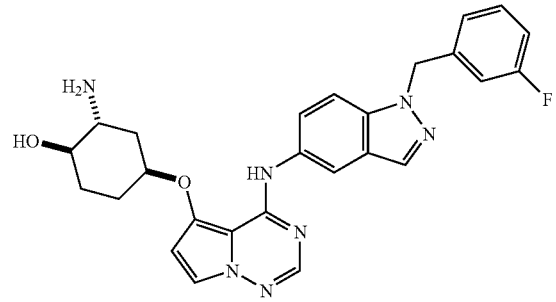

38A. Preparation of trans-(3,4-Epoxy)-cyclohexanol

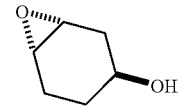

Diethyl azodicarboxylate (1.24 gm, 7.14 mmole) was added to an ice-cooled solution of cis-3,4-epoxy-cyclohexanol (407 mg, 3.57 mmole), triphenylphosphine (1.87 gm, 7.14 mmole) and p-nitrobenzoic acid (1.21 gm, 7.21 mmole) in dry toluene under N₂. After 2 hr, the reaction was diluted with EtOAc, extracted with a saturated aq. solution of NaHCO₃, dried (Na₂SO₄) and the solvent removed. Radial chromatography (silica gel, step gradient elution with hexane containing 10 to 40% EtOAc) afforded trans-(3,4-epoxy)-cyclohexan-(4-nitrobenzoate) (467 mg, 50%) as a solid: MS: 264 (M+H)⁺; HPLC Ret Time: 1.96 min (YMC Xterra S7 3.0×50 mm column, 3 min gradient, 5 mL/min). An stirred, ice-cooled solution of the benzoate (467 mg, 1.77 mmole) in a mixture of dry MeOH (40 mL) and DCM (5 mL) was saturated with NH₃ gas. The bath was removed and the reaction was left stirring at RT overnight. Removal of the solvent followed by radial chromatography (silica gel, step gradient with mixtures of hexane containing 10 to 50% to afford the trans product as an oil (70 mg, 35%): ¹H NMR (CDCl₃) 1.32 (m, 1H), 1.58 (m, 1H), 1.74 (m, 1H), 1.87 (m, 1H), 2.05 (m, 1H), 2.18 (dd, 1H), 2.24 (br s, 1H), 3.11 (m, 2H), 3.77 (s, 1H).

38B. Preparation of N-(1-(3-fluorobenzyl)-1H-indazol-5-yl)-5-((1S,3S,6R) and (1R,3R,6S)-7-oxa-bicyclo[4.1.0]heptan-3-yloxy)pyrrolo[1,2-f][1,2,4]triazin-4-amine

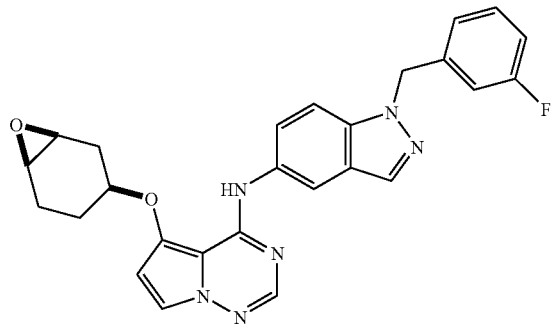

Compound 38B was obtained from 1 and racemic 38A as described for Example 5A and exhibited: MS: 471 (M+H)⁺; HPLC Ret Time: 1.45 min (YMC Xterra S5 3.0×50 mm column, 2 min gradient, 5 mL/min).

38C. Preparation of Regioisomer A, (1S,2S,5S) and (1R,2R,5S)-5-(4-(1-(3-fluorobenzyl)-1H-indazol-5-ylamino)pyrrolo[1,2-f][1,2,4]triazin-5-yloxy)-2-azidocyclohexanol

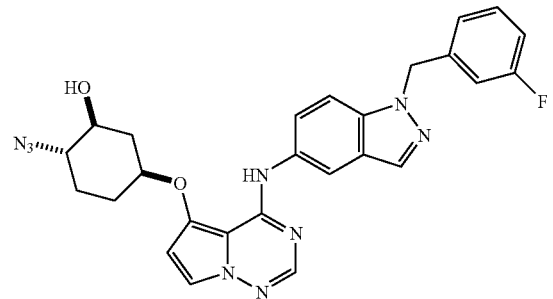

Regioisomer B, (1R,2R,4S) and (1S,2S,4R)-4-(4-(1-(3-fluorobenzyl)-1H-indazol-5-ylamino)pyrrolo[1,2-f][1,2,4]triazin-5-yloxy)-2-azidocyclohexanol

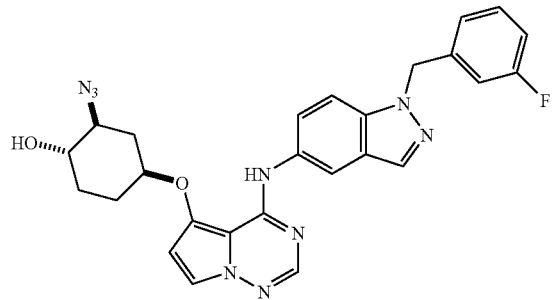

Compounds 38C, isomers A and B, were obtained from racemic 38B (80 mg, 0.170 mmole) and as described for Example 37B and Regioisomer A (25 mg, 30%) exhibited: MS: 514 (M+H)⁺; HPLC Ret Time: 3.78 min (YMC Xterra S5 3.0×50 mm column, eluent: MeOH:H₂O:TFA=1.5:8.5:0.1 to 6.5:3.5:0.1, 6 min gradient, 5 mL/min) and regioisomer B (14 mg, 16%): MS: 514 (M+H)⁺; HPLC Ret Time: 4.02 min (YMC Xterra S5 3.0×50 mm column, eluent: MeOH:H₂O:TFA=1.5:8.5:0.1 to 6.5:3.5:0.1, 6 min gradient, 5 mL/min).

38D. Preparation of (1R,2R,5R) and (1S,2S,5S)-5-(4-(1-(3-fluorobenzyl)-1H-indazol-5-ylamino)pyrrolo[1,2-f][1,2,4]triazin-5-yloxy)-2-aminocyclohexanol Enantiomer A and Enantiomer B Compound 38D, enantiomers A and B, were obtained from racemic 38C, Regioisomer A as described for Example 37D and exhibited: MS: 488 (M+H)⁺; HPLC Ret Time: 1.06 min (YMC Xterra S5 3.0×50 mm column, 2 min gradient, 5 mL/min). A sample was separated by chiral HPLC (Chiralpak AD column, 4.6×250 mm, 10 μm, eluting with mixtures of 0.05% diethylamine in acetonitrile (solvent A) and 0.05% diethylamine in acetonitrile:EtOH=5:95 (solvent B), starting with 5% solvent B for 3 min followed by a gradient varied from 5 to 75% solvent B over 27 min at a flow of 0.9 ml/min to give Enantiomer A: Ret Time: 9.60 min and Enantiomer B: Ret Time: 22.2 min.

38E. Preparation of (1S,2S,4R) and (1R,2R,4S)-4-(4-(1-(3-fluorobenzyl)-1H-indazol-5-ylamino)pyrrolo[1,2-f][1,2,4]triazin-5-yloxy)-2-aminocyclohexanol Compound 38 was obtained from regioisomer B as described for Example 38D and the racemic product exhibited: MS: 488 (M+H)⁺; HPLC Ret Time: 1.16 min (YMC Xterra S7 3.0×50 mm column, 3 min gradient, 5 mL/min).

EXAMPLE 39

Enantiospecific Synthesis of (1R,2R,5S)-5-(4-(1-(3-Fluorobenzyl)-1H-indazol-5-ylamino)pyrrolo[1,2-f][1,2,4]triazin-5-yloxy)-2-aminocyclohexanol

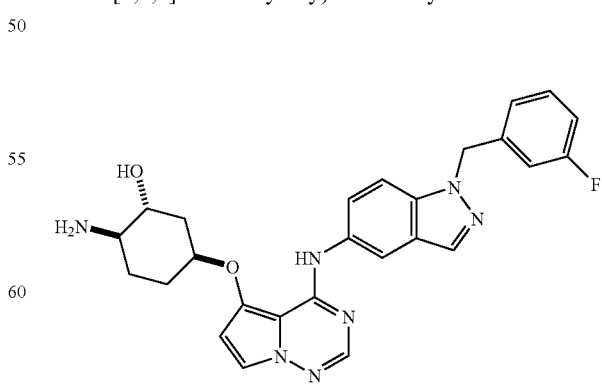

39A. Preparation of (1R,2R,5R)-5-(Benzyloxy)-2-((S)-1-phenylethylamino)cyclohexanol

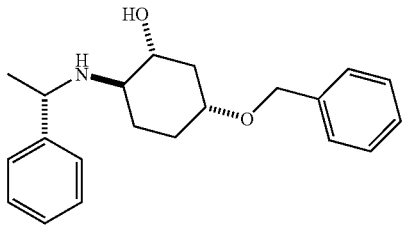

LiClO$_4$ (33.0 gm, 0.31 mole) was added to an ice-cooled, stirred solution of cis-4-benzyloxy-1,2-epoxycyclohexane (12.65 gm, 62.0 mmole, M. Chini et al., J. Org. Chem., 1990, 55, 4265) in dry acetonitrile (137 mL). The bath was removed and (S)-(−)-α-methylbenzylamine (40.0 mL, 0.31 mole, Aldrich, 98% ee) was added after 20 min. The reaction was left stirring at RT overnight, diluted with water, and extracted three times with EtOAc. The combined organic extracts were washed with water, brine and dried (Na$_2$SO$_4$). The solvent was removed on the rotary evaporator and the excess (S)-(−)-α-methylbenzylamine was removed by kugelrohr distillation. Column chromatography [silica gel, step gradient elution starting with hexane/EtOAc/TEA=98/0/2 and ending with 49/49/2] of the residue afforded, in order of elution, (1S,2S,5S)-5-(benzyloxy)-2-((S)-1-phenylethylamino)cyclohexanol) (7.7 gm, 39%) as a solid: [a]$^{25}_{589}$ 0.4 (c 8.0, MeOH), $^1$H NMR (CDCl$_3$) 0.84 (m, 1H), 1.31 (m, 1H), 1.35 (d, 3H), 1.42 (dd, 1H), 1.91 (m, 1H), 2.02 (m, 1H), 2.39 (m, 1H), 2.47 (m, 1H), 3.13 (m, 1H), 3.40 (m, 1H), 3.90 (dd, 1H), 4.54 (dd, 2H), 7.23–7.35 (m, 10H); MS 326 (M+H)$^+$; HPLC Ret Time: 1.86 min (YMC Xterra S5 4.6×50 mm column, 3 min gradient, 4 mL/min) and (1R,2R,2R)-5-(benzyloxy)-2-((S)-1-phenylethylamino)-cyclohexanol) (9.7 gm, 49%) as a solid: [a]$^{25}_{589}$−69.4 (c 4.4, MeOH); $^1$H NMR (CDCl$_3$) 0.90 (m, 1H), 1.22 (m, 2H), 1.34 (d, 3H), 2.04 (m, 2H), 2.15 (m, 1H), 2.38 (m, 1H), 3.16 (m, 1H), 3.37 (m, 1H), 3.96 (dd, 1H), 4.51 (dd, 2H), 7.22–7.29 (m, 10 H); MS 326 (M+H)$^+$; HPLC Ret Time: 1.86 min (YMC Xterra S5 4.6×50 mm column, 3 min gradient, 4 mL/min).

39B. Preparation of tert-Butyl (1R,2R,4R)-2-(tert-butyldimethylsilyloxy)-4-hydroxycyclohexylcarbamate

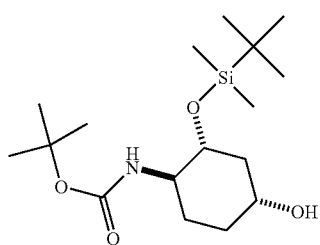

tert-Butyldimethylsilyl trifluoromethanesulfonate (8.8 mL, 38.5 mmole) was added to an ice-cooled, stirred solution of (1R,2R,5R)-5-(benzyloxy)-2-((S)-1-phenylethylamino)-cyclohexanol) (4.8 gm, 14.8 mmole) and TEA (8.2 mL, 59.1 mmole) in dry DCM (250 mL). After 15 min, this was washed with a saturated aq. solution of NaHCO$_3$ and dried (Na$_2$SO$_4$). Removal of the solvent followed by column chromatography (silica gel, step gradient elution with hexane containing 0 to 30% EtOAc) afforded (1R,2R,4R)-4-(benzyloxy)-2-(tert-butyldimethylsilyloxy)-N-((S)-1-phenylethyl)cyclohexanamine (6.2 gm, 95%): MS: 440 (M+H)$^+$; HPLC Ret Time: 2.73 min (YMC Xterra S5 3.0×50 mm column, 3 min gradient, 4 mL/min). A mixture of this material (6.2 gm, 14 mmole), di-tert-butyl dicarbonate (12.2 gm, 56 mmole) and palladium hydroxide (6.5 gm, 20 wt % on carbon, wet) in EtOH (250 mL) was hydrogenated (Paar apparatus, 50 psi H$_2$, 16 hr, RT). Removal of the catalyst and solvent followed by column chromatography (silica gel, step gradient elution with hexane containing 0 to 30% EtOAc) afforded the product (3.3 gm, 68%): [a]$^{25}_{589}$−19.1 (c 5.9, MeOH); $^1$H NMR (CDCl$_3$) 0.11 (s, 3H), 0.13 (s, 3H), 0.78 (s, 9H), 1.20 (m, 1H), 1.33 (s, 9H), 1.46 (m, 1H), 1.53 (m, 1H), 1.64 (m, 1H), 1.89 (m, 1H), 2.06 (m, 1H), 2.7 (br s, 1H), 3.36 (m, 1H), 3.36 (m, 1H), 3.67 (m, 1H), 4.38 (m, 1H); MS 346 (M+H).$^+$

39C. Preparation of (1R,2R,5S)-5-(4-(1-(3-Fluorobenzyl)-1H-indazol-5-ylamino)pyrrolo[1,2-f][1,2,4]triazin-5-yloxy)-2-aminocyclohexanol Powdered 1,1′-azobis(N,N-dimethylformamide) (2.87 gm, 16.7 mmole) was added to a stirred suspension of 4-(1-(3-fluorobenzyl)-1H-indazol-5-ylamino)pyrrolo[1,2-f][1,2,4]triazin-5-ol (2.5 gm, 6.68 mmole, 1), tert-butyl(1R,2R,4R)-2-(tert-butyldimethylsilyloxy)-4-hydroxycyclohexylcarbamate (2.54 gm, 7.35 mmole) and tri-n-butyl phosphine (4.11 mL, 16.7 mmole) in dry toluene (45 mL) under N$_2$ at RT. After 0.5 hr, this was placed in a 60° C. oil bath for 5 hr. The reaction was then diluted with EtOAc, washed with water, brine, and dried (Na$_2$SO$_4$). Removal of the solvents followed by column chromatography (step gradient elution with hexane containing 0 to 20% EtOAc) afforded tert-butyl (1R,2R,4S)-4-(4-(1-(3-fluorobenzyl)-1H-indazol-5-ylamino)pyrrolo[1,2-f][1,2,4]triazin-5-yloxy)-2-(tert-butyldimethylsilyloxy)cyclohexylcarbamate (2.71 gm, 58%), MS: 702 (M+H)$^+$; HPLC Ret Time: 1.99 min (YMC Xterra S5 3.0×50 mm column, 2 min gradient, 5 mL/min). TFA (29 mL) was added to a stirred solution of this material (2.06 gm, 2.93 mmole) in MeOH (29 mL) at RT. After 1.5 hr, the solvents were removed on the rotary evaporator. The residue was dissolved in DCM and the solvent was removed on the rotary evaporator. This was repeated three times. Finally, the residue was dissolved in DCM, washed with a saturated aq. solution of Na$_2$CO$_3$, brine, and dried (Na$_2$SO$_4$). Removal of the solvent followed by column chromatography (step gradient elution with DCM containing 0 to 4% of a 2.0 N solution of NH$_3$ in MeOH) afforded the product (1.14 gm, 80%) which was identical with Example 37, Enantiomer A.

EXAMPLE 40

Enantiospecific Synthesis of (1R,2R,5R)-5-(4-(1-(3-Fluorobenzyl)-1H-indazol-5-ylamino)pyrrolo[1,2-f][1,2,4]triazin-5-yloxy)-2-aminocyclohexanol

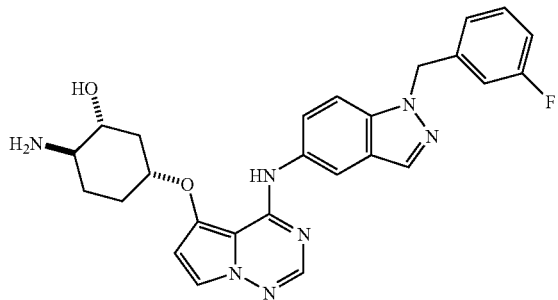

40A. Preparation of tert-Butyl (1R,2R,4S)-2-(tert-butyldimethylsilyloxy)-4-hydroxycyclohexylcarbamate

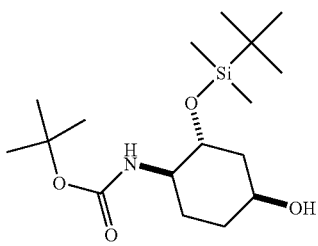

Tetrapropylammonium perruthenate (21 mg, 0.06 mmole) was added to a stirred suspension of N-methylmorpholine N-oxide (107 mg, 0.92 mmole), tert-butyl (1R,2R,4R)-2-(tert-butyldimethylsilyloxy)-4-hydroxycyclohexylcarbamate (39B) (210 mg, 0.61 mmole) and crushed 4 A° molecular sieves (500 mg) in dry $CH_3CN$ (5 mL). After 5 min, the solvent was removed and the residue was suspended in a 1:1 mixture of EtAc and hexane. This was applied onto a short column of silica gel and eluted with five column volumes of the EtAc/hexane mixture. Removal of the solvents left tert-butyl (1R,2R)-2-(tert-butyldimethylsilyloxy)-4-oxocyclohexylcarbamate (189 mg, 90%). This was dissolved in dry THF and the reaction cooled to −78° C. Lithium tri-sec-butylborohydride (1.1 mL, 1.1 mmole, 1.0 M in THF) was added dropwise and the reaction was left stirring for 1 hr after which it allowed to warm to 0° C. A saturated aq. solution of $NH_4Cl$ was carefully added and the reaction was extracted with a mixture of EtOAc/hexane=1/1. The organic extracts were washed with brine and dried ($Na_2SO_4$). Removal of the solvents followed by radial chromatography [silica gel, step gradient elution starting with mixture of hexane containing 0 to 30% EtOAc) afforded, in order of elution, the product (127 mg, 67%) as an oil: 1H NMR ($CDCl_3$) 0.05 (s, 3H), 0.07 (s, 3H), 0.86 (m, 9H), 1.42 (s, 9H), 1.47 (m, 1H), 1.57 (m, 2H), 1.70 (m, 3H), 1.91 (m, 1H), 3.43 (s, 1H), 3.83 (m, 1H), 4.05 (d, 1H), 4.48 (d, 1H) and tert-butyl (1R,2R,4R)-2-(tert-butyldimethylsilyloxy)-4-hydroxycyclohexylcarbamate (9 mg, 5%).

40B. Preparation of (1R,2R,5R)-5-(4-(1-(3-Fluorobenzyl)-1H-indazol-5-ylamino)pyrrolo[1,2-f][1,2,4]triazin-5-yloxy)-2-aminocyclohexanol tert-Butyl (1R,2R,4R)-4-(4-(1-(3-fluorobenzyl)-1H-indazol-5-ylamino)pyrrolo[1,2-f][1,2,4]triazin-5-yloxy)-2-(tert-butyldimethylsilyloxy)-cyclohexylcarbamate was obtained from 1 and 40A as described in 39C. It was then deprotected as described in 39C to give the product which was identical with Example 38, Enantiomer A.

EXAMPLE 41

Enantiospecific Synthesis of (1S,2S,5R)-5-(4-(1-(3-Fluorobenzyl)-1H-indazol-5-ylamino)pyrrolo[1,2-f][1,2,4]triazin-5-yloxy)-2-aminocyclohexanol

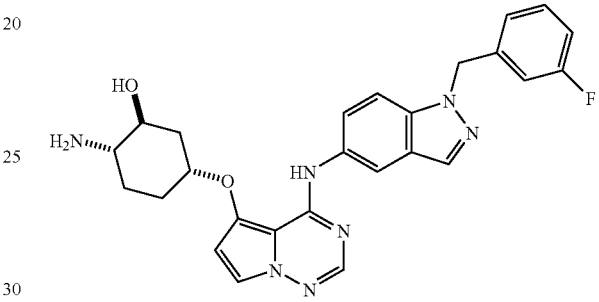

41A. Preparation of tert-Butyl(1S,2S,4S)-2-(tert-butyldimethylsilyloxy)-4-hydroxycyclohexylcarbamate

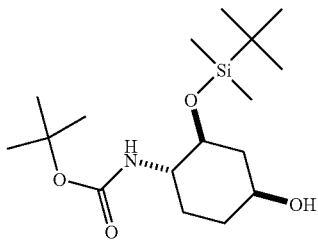

(1S,2S,4S)-4-(Benzyloxy)-2-(tert-butyldimethylsilyloxy)-N-((S)-1-phenylethyl)cyclohexanamine MS: 440 (M+H)+; HPLC Ret Time: 2.83 min (YMC Xterra S5 4.6×50 mm column, 3 min gradient, 4 mL/min) was obtained from (1S,2S,5S)-5-(benzyloxy)-2-((S)-1-phenylethylamino)-cyclohexanol) 39A as described in 39B. It was then converted to the product as described in 39B and exhibited an $[a]^{25}_{589}$ 19.2 (c 5.7, MeOH).

41B. Preparation of (1S,2S,5R)-5-(4-(1-(3-fluorobenzyl)-1H-indazol-5-ylamino)pyrrolo[1,2-f][1,2,4]triazin-5-yloxy)-2-aminocyclohexanol tert-Butyl(1S,2S,4R)-4-(4-(1-(3-fluorobenzyl)-1H-indazol-5-ylamino)pyrrolo[1,2-f][1,2,4]triazin-5-yloxy)-2-(tert-butyldimethylsilyloxy)-cyclohexylcarbamate was obtained from 1 and 41A as described for in 39C. It was then deprotected as described in 39C to give the product which was identical with Example 37, Enantiomer B.

EXAMPLE 42

Enantiospecific Synthesis of (1S,2S,5S)-5-(4-(1-(3-Fluorobenzyl)-1H-indazol-5-ylamino)pyrrolo[1,2-f][1,2,4]triazin-5-yloxy)-2-aminocyclohexanol

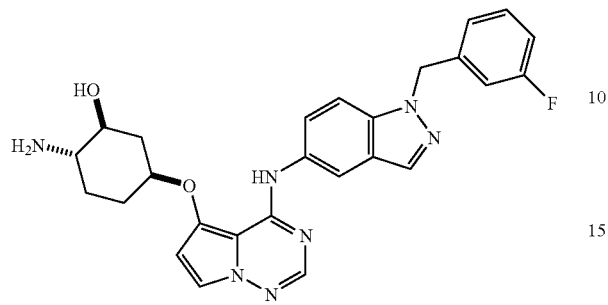

42A. Preparation of tert-Butyl (1S,2S,4R)-2-(tert-butyldimethylsilyloxy)-4-hydroxycyclohexylcarbamate

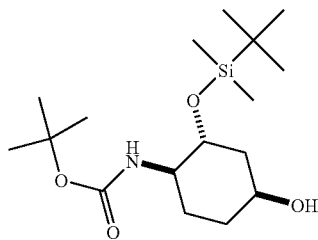

tert-Butyl (1S,2S)-2-(tert-butyldimethylsilyloxy)-4-oxo-cyclohexylcarbamate was prepared from tert-butyl (1S,2S,4S)-2-(tert-butyldimethylsilyloxy)-4-hydroxycyclohexylcarbamate (41A) as described in 40A. It was converted to the product as described in 40A.

42B. Preparation of (1S,2S,5S)-5-(4-(1-(3-Fluorobenzyl)-1H-indazol-5-ylamino)pyrrolo[1,2-f][1,2,4]triazin-5-yloxy)-2-aminocyclohexanol tert-Butyl (1S,2S,4S)4-(4-(1-(3-fluorobenzyl)-1H-indazol-5-ylamino)pyrrolo[1,2-f][1,2,4]triazin-5-yloxy)-2-(tert-butyldimethylsilyloxy)-cyclohexylcarbamate was obtained from 1 and 42A as described for in 39C. It was then deprotected as described in 39C to give the product which was identical with Example 38, Enantiomer B.

EXAMPLE 43

(1R,2R,5S)-2-amino-5-(4-(3-methoxyphenylamino)pyrrolo[1,2-f][1,2,4]triazin-5-yloxy)cyclohexanol

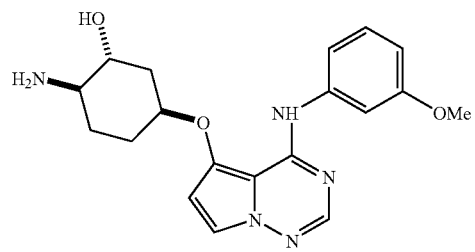

43A. Preparation 4-(3-Methoxyphenylamino)pyrrolo[1,2-f][1,2,4]triazin-5-ol

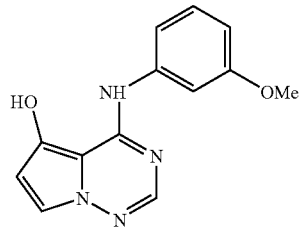

Compound 43A was prepared from 1F and 3-methoxyaniline in the same manner as 1G and exhibited: MS: 257 (M+H)+; HPLC Ret Time: 1.22 min (YMC Xterra S5 4.6×50 mm column, 3 min gradient, 4 mL/min).

43B: Preparation of (1R,2R,5S)-2-Amino-5-(4-(3-methoxyphenylamino)-pyrrolo[1,2-f][1,2,4]triazin-5-yloxy)cyclohexanol Compound 43 was prepared from 43A and tert-butyl (1R,2R,4R)-2-(tert-butyldimethylsilyloxy)-4-hydroxycyclohexylcarbamate (39B) in the same manner as described for 39C and exhibited: MS: 370 (M+H)+; HPLC Ret Time: 1.44 min (Phenomenex-Luna S5, 4.6×50 mm column, 3 min gradient, 4 mL/min).

EXAMPLE 44

(1S,2S,5S)-2-Amino-5-(4-(3-methoxyphenylamino)pyrrolo[1,2-f][1,2,4]triazin-5-yloxy)cyclohexanol

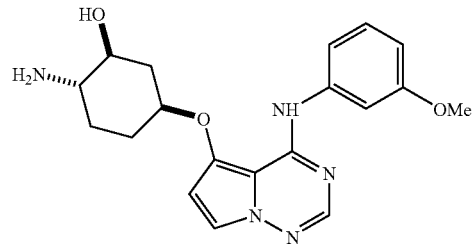

Compound 44 was prepared from 4-(3-methoxyphenylamino)pyrrolo[1,2-f][1,2,4]triazin-5-ol (43A) and tert-butyl (1S,2S,4R)-2-(tert-butyldimethylsilyloxy)-4-hydroxycyclohexylcarbamate (42A) in the same manner as described for 39C and exhibited: MS: 370 (M+H)+; HPLC Ret Time: 0.79 min (YMC Xterra S7, 3.0×50 mm column, 2 min gradient, 5 mL/min).

EXAMPLE 45

(1R,2R,5S)-2-Amino-5-(4-(3-ethynylphenylamino)pyrrolo[1,2-f][1,2,4]triazin-5-yloxy)cyclohexanol

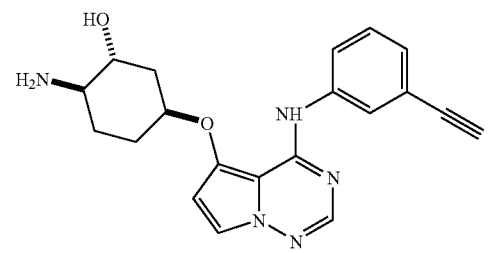

45A. Preparation 4-(3-Ethynylphenylamino)pyrrolo [1,2-f][1,2,4]triazin-5-ol

Compound 45A was prepared from 1F and 3-ethynylbenzenamine in the same manner as 1G and exhibited: MS: 251 (M+H)$^+$; HPLC Ret Time: 1.39 min (YMC Xterra S5 4.6×50 mm column, 3 min gradient, 4 mL/min).

45B: Preparation of (1R,2R,5S)-2-Amino-5-(4-(3-ethynylphenylamino)-pyrrolo[1,2-f][1,2,4]triazin-5-yloxy)cyclohexanol Compound 45 was prepared from 45A and tert-butyl (1R,2R,4R)-2-(tert-butyldimethylsilyloxy)-4-hydroxycyclohexylcarbamate (39B) in the same manner as described for 39C and exhibited: MS: 364 (M+H)$^+$; HPLC Ret Time: 1.63 min (YMC Xterra S5, 4.6×50 mm column, 3 min gradient, 4 mL/min).

EXAMPLE 46

(1S,2S,5S)-2-Amino-5-(4-(3-ethynylphenylamino) pyrrolo[1,2-f][1,2,4]triazin-5-yloxy)cyclohexanol Compound 46 was prepared from 45A and tert-butyl(1S, 2S,4R)-2-(tert-butyldimethylsilyloxy)-4-hydroxycyclohexylcarbamate (42A) in the same manner as described for 39C and exhibited: MS: 364 (M+H)$^+$; HPLC Ret Time: 0.97 min (YMC Xterra S7, 3.0×50 mm column, 2 min gradient, 5 mL/min).

EXAMPLE 47

(1S,2S,5R)-2-Amino-5-(4-(3-ethynylphenylamino) pyrrolo[1,2-f][1,2,4]triazin-5-yloxy)cyclohexanol Compound 47 was prepared from 45A and tert-butyl(1S, 2S,4S)-2-(tert-butyldimethylsilyloxy)-4-hydroxycyclohexylcarbamate (41A) in the same manner as described for 39C and exhibited: MS: 364 (M+H)$^+$; HPLC Ret Time: 0.98 min (YMC Xterra S7, 3.0×50 mm column, 2 min gradient, 5 mL/min).

EXAMPLE 48

(1R,2R,5R)-2-Amino-5-(4-(3-ethynylphenylamino) pyrrolo[1,2-f][1,2,4]triazin-5-yloxy)cyclohexanol Compound 48 was prepared from 45A and tert-butyl(1R, 2R,4S)-2-(tert-butyldimethylsilyloxy)-4-hydroxycyclohexylcarbamate (40A) in the same manner as described for 39C and exhibited: MS: 364 (M+H)$^+$; HPLC Ret Time: 0.98 min (YMC Xterra S7, 3.0×50 mm column, 2 min gradient, 5 mL/min).

EXAMPLE 49

(1R,2R,5S)-2-Amino-5-(4-(3-bromophenylamino) pyrrolo[1,2-f][1,2,4]triazin-5-yloxy)cyclohexanol

49A. Preparation 4-(3-Bromophenylamino)pyrrolo[1,2-f][1,2,4]triazin-5-ol

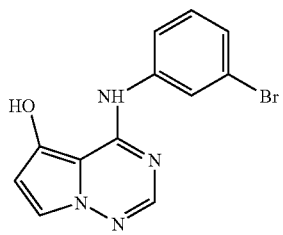

Compound 49A was prepared from 1F and 3-bromoaniline in the same manner as 1G and exhibited: MS: 306 (M+H)$^+$; HPLC Ret Time: 1.64 min (YMC Xterra S5 4.6×50 mm column, 3 min gradient, 4 mL/min).

49B: Preparation of (1R,2R,5S)-2-Amino-5-(4-(3-bromophenylamino)-pyrrolo[1,2-f][1,2,4]triazin-5-yloxy)cyclohexanol Compound 49 was prepared from 49A and tert-butyl(1R,2R,4R)-2-(tert-butyldimethylsilyloxy)-4-hydroxycyclohexylcarbamate (39B) in the same manner as described for 39C and exhibited: MS: 418 (M+H)$^+$; HPLC Ret Time: 1.89 min (YMC Xterra S5, 4.6×50 mm column, 3 min gradient, 4 mL/min).

EXAMPLE 50

(1R,2R,5S)-2-Amino-5-(4-(3-chlorophenylamino)pyrrolo[1,2-f][1,2,4]triazin-5-yloxy)cyclohexanol

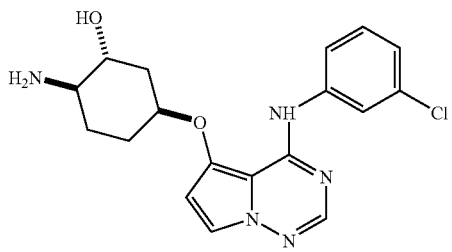

50A. Preparation 4-(3-Chlorophenylamino)pyrrolo[1,2-f][1,2,4]triazin-5-ol

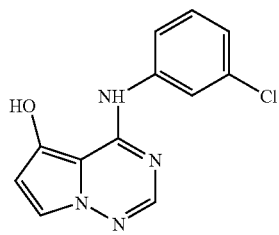

Compound 50A was prepared from 1F and 3-chloroaniline in the same manner as 1G and exhibited: MS: 261 (M+H)$^+$; HPLC Ret Time: 1.28 min (YMC Xterra S5 4.6×50 mm column, 3 min gradient, 4 mL/min).

50B: Preparation of (1R,2R,5S)-2-Amino-5-(4-(3-chlorophenylamino)-pyrrolo[1,2-f][1,2,4]triazin-5-yloxy)cyclohexanol Compound 50 was prepared from 50A and tert-butyl (1R,2R,4R)-2-(tert-butyldimethylsilyloxy)-4-hydroxycyclohexylcarbamate (39B) in the same manner as described for 39C and exhibited: MS: 374 (M+H)$^+$; HPLC Ret Time: 1.90 min (YMC Xterra S5, 4.6×50 mm column, 3 min gradient, 4 mL/min).

EXAMPLE 51

(1R,2R,5S)-2-Amino-5-(4-(3-chloro-4-fluorophenylamino)pyrrolo[1,2-f][1,2,4]triazin-5-yloxy)cyclohexanol

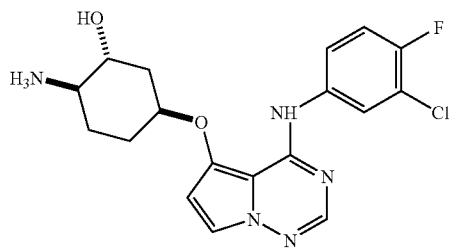

Compound 51 was prepared from 7A and tert-butyl (1R,2R,4R)-2-(tert-butyldimethylsilyloxy)-4-hydroxycyclohexylcarbamate (39B) in the same manner as described for 39C and exhibited: MS: 392 (M+H)$^+$; HPLC Ret Time: 1.72 min (Phenomenex-Luna S5, 3.0×50 mm column, 3 min gradient, 4 mL/min).

What is claimed is:
1. A compound of formula I

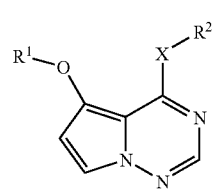

(I)

wherein

R$^1$ is hydrogen, alkyl, substituted alkyl, cycloalkyl, substituted cycloalkyl, carbocyclic ring, substituted carbocyclic ring, aryl, substituted aryl, heterocyclyl or substituted heterocyclyl; said substituents on the substituted alkyl, cycloalkyl, aryl or heterocyclyl selected from the group consisting of one or more hydrogen, halogen, alkyl, substituted alkyl, aryl, substituted aryl, heterocyclyl, substituted heterocyclyl, —CN, —N$_3$, —NH$_2$, —NH-alkyl, —NH-substituted alkyl, —NH-aryl, —NH-substituted aryl, —NHCOalkyl, imino, alkyl imino, substituted alkyl imino, aryl imino, substituted aryl imino, hydroxyl, alkoxy, substituted alkoxy, aryloxy, substituted aryloxy, carboxy, —CONHalkyl, —CONHsubstituted alkyl, R² is aryl, substituted aryl, heterocyclyl or substituted heterocyclyl; said substituents on the substituted aryl or substituted heterocyclyl group are selected from the group consisting of one or more hydrogen, halogen, alkyl, substituted alkyl, cycloalkyl, substituted cycloalkyl, alkenyl, substituted alkenyl, alkynyl, substituted alkynyl, —CN, —N₃, alkoxy, substituted alkoxy, aryl, substituted aryl, aryloxy, substituted aryloxy, —O-heterocyclyl, —O-substituted heterocyclyl, heterocyclyl, substituted heterocyclyl, —CF₃, and —OCF₃;

X is a direct bond or —NH—;

with the proviso that R¹ is not methyl;

or a pharmaceutically acceptable salt or stereoisomer thereof.

2. The compound as defined in claim 1 wherein
- R¹ is cycloalkyl or substituted cycloalkyl, said substituents on the substituted cycloalkyl selected from the group consisting of one or more —OH, —NH₂, —NHCN, ═O, —NHalkylSO₂alkyl, —NHalkylarylCO₂alkyl, —NHalkylarylCO₂H, —NHalkylCO₂H, —NHarylalkylCO₂H, —NHalkylarylSO₂NHCOalkyl, —NHalkylaryl-NHalkylarylSO₂NHCOalky, —NHalkylarylCONHSO₂alkyl and —NHCOalkylamino;
- R² is aryl, substituted aryl, heterocyclyl or substituted heterocyclyl, said substituents on the substituted aryl or heterocyclyl selected from the group consisting of one or more hydrogen, halogen, alkylaryl or substituted alkylaryl; and
- X is —NH—.

3. The compound as defined in claim 1 wherein
- R¹ is cyclohexyl or substituted cyclohexyl, said substituents on the substituted cycloalkyl selected from the group consisting of one or more —OH, —NH₂, —NHCN, ═O, —NHalkylSO₂alkyl, —NHalkylarylCO₂alkyl, —NHalkylarylCO₂H, —NHalkylCO₂H, —NHarylalkylCO₂H, —NHalkylarylSO₂NHCOalkyl, —NHalkylaryl—NHalkylarylSO₂NHCOalky, —NHalkylarylCONHSO₂alkyl and —NHCOalkylamino.

4. The compound which is
- (1,4-cis)-4-(4-(1-(3-Fluorobenzyl)-1H-indazol-5-ylamino)pyrrolo[1,2-f][1,2,4]triazin-5-yloxy)cyclohexanol;
- 1-(3-Fluorobenzyl)-N-(5-((1,4-cis)-4-aminocyclohexyloxy)H-pyrrolo[1,2-b]pyridazin-4-yl)-1H-indazol-5-amine;
- 1-(3-Fluorobenzyl)-N-(5-((1,4-trans)-4-aminocyclohexyloxy) H-pyrrolo[1,2-b]pyridazin-4-yl)-1H-indazol-5-amine;
- 5-((1,4-cis)-4-Aminocyclohexyloxy)-N-(3-chloro-4-fluorophenyl)pyrrolo[1,2-f][1,2,4]triazin-4-amine;
- N-(1-(3-Fluorobenzyl)- 1H-indazol-5-yl)-5-((1,4-cis)-4-(2-(methylsulfonyl)-ethylamino)cyclohexyloxy)pyrrolo[1,2-f][1,2,4]triazin-4-amine-N-(1-(3-Fluorobenzyl)-1H-indazol-5-yl)-5-((1,4-trans)-4-(2-(methylsulfonyl)ethylamino)cyclohexyloxy)pyrrolo[1,2-f][1,2,4]triazin-4-amine;
- 4-(((1,4-trans)-4-(4-(1-(3-Fluorobenzyl)-1H-indazol-5-ylamino)pyrrolo[1,2-f][1,2,4]triazin-5-yloxy)cyclohexylamino)methyl)benzoic acid;
- 4-(((1,4-cis)-4-(4-(1-(3-Fluorobenzyl)-1H-indazol-5-ylamino)pyrrolo[1,2-f][1,2,4]triazin-5-yloxy)cyclohexylamino)methyl)benzoic acid;
- 4-(((1,4-trans)-4-(4-(3-chloro-4-(pyridin-2-ylmethoxy) phenylamino)pyrrolo-[1,2-f][1,2,4]triazin-5-yloxy)cyclohexylamino)methyl)benzoic acid;
- 4-(((1,4-cis)-4-(4-(3-chloro-4-(pyridin-2-ylmethoxy) phenylamino)pyrrolo-[1,2-f][1,2,4]triazin-5-yloxy)cyclohexylamino)methyl)benzoic acid; 1-(4-(4-(1-(3-fluorobenzyl)-1H-indazol-5-ylamino)pyrrolo[1,2-f][1,2,4]triazin-5-yloxy)cyclohexylamino) cyclopropanecarboxylic acid, isomer A and B;
- 4-(((1,4-trans)-4-(4-(1-(3-Fluorobenzyl)-1H-indazol-5-ylamino)pyrrolo[1,2-f][1,2,4]triazin-5-yloxy)cyclohexylamino)methyl)-N-(methylsulfonyl)benzamide;
- N-((1,4-cis)-4-(4-(1-(3-Fluorobenzyl)-1H-indazol-5-ylamino)pyrrolo[1,2-f][1,2,4]triazin-5-yloxy)cyclohexyl)-2-aminoacetamide;
- N-((1,4-trans)-4-(4-(1-(3-Fluorobenzyl)-1H-indazol-5-ylamino)pyrrolo[1,2-f][1,2,4]triazin-5-yloxy)cyclohexyl)-2-aminoacetamide; 1-(4-(4-(1-(3-Fluorobenzyl)-1H-indazol-5-ylamino)pyrrolo[1,2-f][1,2,4] triazin-5-yloxy)piperidin-1-yl)-2-aminoethanone;
- (1R,2R,5S)- and (1S,2S,5R)-5-(4-(1-(3-fluorobenzyl)-1H-indazol-5-ylamino)pyrrolo[1,2-f][1,2,4]triazin-5-yloxy)-2-aminocyclohexanol;
- (1R,2R,5R) and (1S,2S,5S)-5-(4-(1-(3-fluorobenzyl)-1H-indazol-5-ylamino)pyrrolo[1,2-f][1,2,4]triazin-5-yloxy)-2-aminocyclohexanol;

or a pharmaceutically acceptable salts thereof.

5. A pharmaceutical composition comprising one or more compounds of claim 1 and a pharmaceutically acceptable carrier.

* * * * *

UNITED STATES PATENT AND TRADEMARK OFFICE
CERTIFICATE OF CORRECTION

PATENT NO. : 7,102,003 B2
APPLICATION NO. : 11/157460
DATED : September 5, 2006
INVENTOR(S) : Gavai et al.

It is certified that error appears in the above-identified patent and that said Letters Patent is hereby corrected as shown below:

In Column 62, Lines 6-11:
"N-(1-(3-Fluorobenzyl)- 1H-indazol-5-yl)-5-((1,4-*cis*)-4-(2-(methylsulfonyl)-ethylamino)cyclohexyloxy)pyrrolo[1,2-f][1,2,4]triazin-4-amine; N-(1-(3-Fluorobenzyl)-1H-indazol-5-yl)-5-((1,4-*trans*)-4-(2-(methylsulfonyl)ethylamino) cyclohexyloxy)pyrrolo[1,2-f][1,2,4]triazin-4-amine;"

Should read :

-- **N-(1-(3-Fluorobenzyl)-1H-indazol-5-yl)-5-((1,4-*cis*)-4-(2-(methylsulfonyl)-ethylamino)cyclohexyloxy)pyrrolo[1,2-f][1,2,4]triazin-4-amine;**

**N-(1-(3-Fluorobenzyl)-1H-indazol-5-yl)-5-((1,4-*trans*)-4-(2-(methylsulfonyl)ethylamino)cyclohexyloxy)pyrrolo[1,2-f][1,2,4]triazin-4-amine;** --

In Column 62, Lines 21-26: "4-(((1,4-*cis*)-4-(4-(3-chloro-4-(pyrid in-2-ylmethoxy) phenylamino)pyrrolo-[1,2-f][1,2,4]triazin-5-yloxy)cyclohexylamino)methyl)benzoic acid; 1-(4-(4-(1-(3-fluorobenzyl)-1H-indazol-5-ylamino)pyrrolo[1,2-f][1,2,4]triazin-5-yloxy)cyclohexylamino) cyclopropanecarboxylic acid, isomer A and B;"

Should read:

-- 4-(((1,4-*cis*)-4-(4-(3-chloro-4-(pyridin-2-ylmethoxy)phenylamino) pyrrolo-[1,2-f][1,2,4]triazin-5-yloxy)cyclohexylamino)methyl)benzoic acid;

1-(4-(4-(1-(3-fluorobenzyl)-1H-indazol-5-ylamino)pyrrolo[1,2-f][1,2,4] triazin-5-yloxy)cyclohexylamino)cyclopropanecarboxylic acid, isomer A and B; --

UNITED STATES PATENT AND TRADEMARK OFFICE
CERTIFICATE OF CORRECTION

PATENT NO. : 7,102,003 B2
APPLICATION NO. : 11/157460
DATED : September 5, 2006
INVENTOR(S) : Gavai et al.

It is certified that error appears in the above-identified patent and that said Letters Patent is hereby corrected as shown below:

In Column 62, Lines 33-37: "N-((1,4-*trans*)-4-(4-(1-(3-Fluorobenzyl)-1H-indazol-5-ylamino)pyrrolo[1,2-f][1,2,4]triazin-5-yloxy)cyclohexyl)-2-aminoacetamide; 1-(4-(4-(1-(3-Fluorobenzyl)-1H-indazol-5-ylamino)pyrrolo[1,2-f][1,2,4]triazin-5-yloxy)piperidin-1-yl)-2-aminoethanone;

should read:

--**N-((1,4-*trans*)-4-(4-(1-(3-Fluorobenzyl)-1H-indazol-5-ylamino)pyrrolo[1,2-f][1,2,4]triazin-5-yloxy)cyclohexyl)-2-aminoacetamide;**

1-(4-(4-(1-(3-Fluorobenzyl)-1H-indazol-5-ylamino)pyrrolo[1,2-f][1,2,4]triazin-5-yloxy)piperidin-1-yl)-2-aminoethanone; --

Signed and Sealed this

Thirteenth Day of February, 2007

JON W. DUDAS
*Director of the United States Patent and Trademark Office*